United States Patent
Trudel et al.

(10) Patent No.: US 11,457,819 B2
(45) Date of Patent: Oct. 4, 2022

(54) SYSTEMS AND METHODS FOR MONITORING AND EVALUATING NEUROMODULATION THERAPY

(71) Applicant: Medtronic Ardian Luxembourg S.a.r.l., Luxembourg (LU)

(72) Inventors: Julie Trudel, Santa Rosa, CA (US); Douglas Hettrick, Andover, MN (US)

(73) Assignee: MEDTRONIC ARDIAN LUXEMBOURG S.A.R.L., Luxembourg (LU)

( * ) Notice: Subject to any disclaimer, the term of this patent is extended or adjusted under 35 U.S.C. 154(b) by 211 days.

(21) Appl. No.: 16/883,626

(22) Filed: May 26, 2020

(65) Prior Publication Data
US 2020/0281476 A1 Sep. 10, 2020

Related U.S. Application Data

(63) Continuation of application No. 15/421,119, filed on Jan. 31, 2017, now abandoned.
(Continued)

(51) Int. Cl.
*A61N 7/00* (2006.01)
*A61B 5/00* (2006.01)
(Continued)

(52) U.S. Cl.
CPC ............. *A61B 5/0084* (2013.01); *A61B 5/01* (2013.01); *A61B 5/021* (2013.01); *A61B 5/026* (2013.01);
(Continued)

(58) Field of Classification Search
CPC ...... A61B 18/1492; A61B 2018/00577; A61B 5/0084; A61B 5/01; A61B 5/021;
(Continued)

(56) References Cited

U.S. PATENT DOCUMENTS

| 4,709,698 A | 12/1987 | Johnston et al. |
| 5,425,364 A | 6/1995 | Imran |

(Continued)

FOREIGN PATENT DOCUMENTS

| WO | 2012/061159 A1 | 5/2012 |
| WO | 2014160832 A2 | 10/2014 |

(Continued)

OTHER PUBLICATIONS

Wikipedia, Pulse wave velocity, 2022; https://en.wikipedia.org/wiki/Pulse_wave_velocity#Using_pressure-flow_velocity,_pressure-volumetric_flow_relationships_or_characteristic_impedance (Year: 2022).*

(Continued)

*Primary Examiner* — Jonathan T Kuo
(74) *Attorney, Agent, or Firm* — Shumaker & Sieffert, P.A.

(57) ABSTRACT

Systems and methods for informing and evaluating neuromodulation therapy are disclosed herein. A system configured in accordance with embodiments of the present technology can include, for example, a guidewire having a proximal portion, a distal portion configured to be positioned at a target site in a blood vessel of a human patient, and a sensing element positioned along the distal portion. The sensing element can be a pressure sensing element, a flow sensing element, an impedance sensing element, and/or a temperature sensing element. The system can further include a controller configured to obtain one or more measurements related to a physiological parameter of the patient via the sensing element. Based on the measurements, the controller can determine the physiological parameter and compare the parameter to a predetermined threshold. Based on the comparison, the controller and/or the operator can (Continued)

assess the likelihood of the patient benefiting from neuromodulation therapy.

20 Claims, 12 Drawing Sheets

Related U.S. Application Data

(60) Provisional application No. 62/346,710, filed on Jun. 7, 2016, provisional application No. 62/289,739, filed on Feb. 1, 2016.

(51) Int. Cl.
| | | |
|---|---|---|
| *A61B 5/026* | (2006.01) | |
| *A61B 5/0215* | (2006.01) | |
| *A61B 5/053* | (2021.01) | |
| *A61B 5/20* | (2006.01) | |
| *A61N 1/36* | (2006.01) | |
| *G16H 20/40* | (2018.01) | |
| *G16H 40/63* | (2018.01) | |
| *G16H 50/20* | (2018.01) | |
| *G16H 20/30* | (2018.01) | |
| *A61B 5/01* | (2006.01) | |
| *A61B 5/021* | (2006.01) | |
| *A61B 5/0285* | (2006.01) | |
| *A61B 5/0538* | (2021.01) | |
| *A61B 18/14* | (2006.01) | |
| *A61M 25/00* | (2006.01) | |
| *A61N 5/04* | (2006.01) | |
| *A61N 5/06* | (2006.01) | |
| *A61N 7/02* | (2006.01) | |
| *A61B 18/00* | (2006.01) | |

(52) U.S. Cl.
CPC .......... *A61B 5/0215* (2013.01); *A61B 5/0285* (2013.01); *A61B 5/053* (2013.01); *A61B 5/0538* (2013.01); *A61B 5/201* (2013.01); *A61B 5/4833* (2013.01); *A61B 5/4848* (2013.01); *A61B 5/6851* (2013.01); *A61B 5/7232* (2013.01); *A61B 18/1492* (2013.01); *A61M 25/0026* (2013.01); *A61N 1/36* (2013.01); *A61N 1/3606* (2013.01); *A61N 1/36114* (2013.01); *A61N 5/045* (2013.01); *A61N 5/0622* (2013.01); *A61N 7/02* (2013.01); *G16H 20/30* (2018.01); *G16H 20/40* (2018.01); *G16H 40/63* (2018.01); *G16H 50/20* (2018.01); *A61B 2018/00577* (2013.01); *A61N 2007/0026* (2013.01)

(58) Field of Classification Search
CPC ..... A61B 5/0215; A61B 5/026; A61B 5/0285; A61B 5/053; A61B 5/0538; A61B 5/201; A61B 5/4833; A61B 5/4848; A61B 5/6851; A61B 5/7232; A61M 25/0026; A61N 1/36; A61N 1/3606; A61N 1/36114; A61N 2007/0026; A61N 5/045; A61N 5/0622; A61N 7/02; G16H 20/30; G16H 20/40; G16H 40/63; G16H 50/20
See application file for complete search history.

(56) References Cited

U.S. PATENT DOCUMENTS

| | | |
|---|---|---|
| 8,777,942 B2 | 7/2014 | Wu et al. |
| 8,998,894 B2 | 4/2015 | Mauch et al. |
| 9,060,755 B2 | 6/2015 | Buckley et al. |
| 9,084,610 B2 | 7/2015 | Goshgarian et al. |
| 9,327,123 B2 | 5/2016 | Yamasaki et al. |
| 2006/0100618 A1 | 5/2006 | Chan et al. |
| 2011/0112400 A1 | 5/2011 | Emery et al. |
| 2014/0012133 A1* | 1/2014 | Sverdlik ............... A61B 5/026 600/587 |
| 2014/0249520 A1 | 9/2014 | Ghaffari et al. |
| 2016/0029960 A1* | 2/2016 | Toth ....................... A61N 1/05 606/41 |

FOREIGN PATENT DOCUMENTS

| | | |
|---|---|---|
| WO | 2015/061624 A1 | 4/2015 |
| WO | 2016/054379 A1 | 4/2016 |

OTHER PUBLICATIONS

Second Office Action, and machine translation thereof, from counterpart Chinese Application No. 201780009142.6, dated Jun. 9, 2021, 28 pp.

Alastruey et al., "Numerical Assessment of Time-Domain Methods for the Estimation of Local Arterial Pulse Wave Speed," Journal of Biomechanics, vol. 44, No. 5, Mar. 15, 2011, pp. 885-891.

International Preliminary Report on Patentability from International Application No. PCT/US2017/015887, dated Aug. 7, 2018, 09 pp.

Mark R. de Jong et al. "Renal Nerve Stimulation-Induced Blood Pressure Changes Predict Ambulatory Blood Pressure Response After Renal Denervation" Mar. 9, 2016, Hypertension 2016; 68:707-714.

* cited by examiner

SYSTEMS AND METHODS FOR MONITORING AND EVALUATING NEUROMODULATION THERAPY

CROSS-REFERENCE TO RELATED APPLICATION(S)

The present application is a continuation application of U.S. application Ser. No. 15/421,119, filed Jan. 31, 2017, which claims the benefit of U.S. Provisional Patent Application No. 62/289,739, filed Feb. 1, 2016, and U.S. Provisional Patent Application No. 62/346,710, filed Jun. 7, 2016, all of which are incorporated herein by reference in their entireties.

TECHNICAL FIELD

The present technology is related to neuromodulation. In particular, various embodiments of the present technology are related to systems and methods for identifying responders to neuromodulation therapy and/or assessing the efficacy of neuromodulation therapy.

BACKGROUND

The sympathetic nervous system (SNS) is a primarily involuntary bodily control system typically associated with stress responses. Fibers of the SNS extend through tissue in almost every organ system of the human body and can affect characteristics such as pupil diameter, gut motility, and urinary output. Such regulation can have adaptive utility in maintaining homeostasis or in preparing the body for rapid response to environmental factors. Chronic over-activation of the SNS, however, is a common maladaptive response that can drive the progression of many disease states. Excessive activation of the renal SNS in particular has been identified experimentally and in humans as a likely contributor to the complex pathophysiology of arrhythmias, hypertension, states of volume overload (e.g., heart failure), and progressive renal disease.

Sympathetic nerves of the kidneys terminate in the renal blood vessels, the juxtaglomerular apparatus, and the renal tubules, among other structures. Stimulation of the renal sympathetic nerves can cause, for example, increased renin release, increased sodium reabsorption, and reduced renal blood flow. These and other neural-regulated components of renal function are considerably stimulated in disease states characterized by heightened sympathetic tone. For example, reduced renal blood flow and glomerular filtration rate as a result of renal sympathetic efferent stimulation is likely a cornerstone of the loss of renal function in cardio-renal syndrome, (i.e., renal dysfunction as a progressive complication of chronic heart failure). Pharmacologic strategies to thwart the consequences of renal sympathetic stimulation include centrally-acting sympatholytic drugs, beta blockers (e.g., to reduce renin release), angiotensin-converting enzyme inhibitors and receptor blockers (e.g., to block the action of angiotensin II and aldosterone activation consequent to renin release), and diuretics (e.g., to counter the renal sympathetic mediated sodium and water retention). These pharmacologic strategies, however, have significant limitations including limited efficacy, compliance issues, side effects, and others.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Systems and methods in accordance with embodiments of the present technology can be configured to detect physiological parameters before, during, and/or after neuromodulation therapy. This information can be used to (1) predict a particular patient's likelihood of deriving a therapeutic benefit from neuromodulation therapy ("responsiveness"), and/or (2) assess the efficacy of a given neuromodulation therapy. Specific details of several embodiments of the present technology are described herein with reference to FIGS. 1A-13. Although many of the embodiments are described with respect to devices, systems, and methods for intravascular renal neuromodulation, other applications and other embodiments in addition to those described herein are within the scope of the present technology. For example, at least some embodiments of the present technology may be useful for intraluminal neuromodulation, extravascular neuromodulation, non-renal neuromodulation, and/or therapies other than neuromodulation. It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device. The headings provided herein are for convenience only and should not be construed as limiting the subject matter disclosed.

Figure 1A:
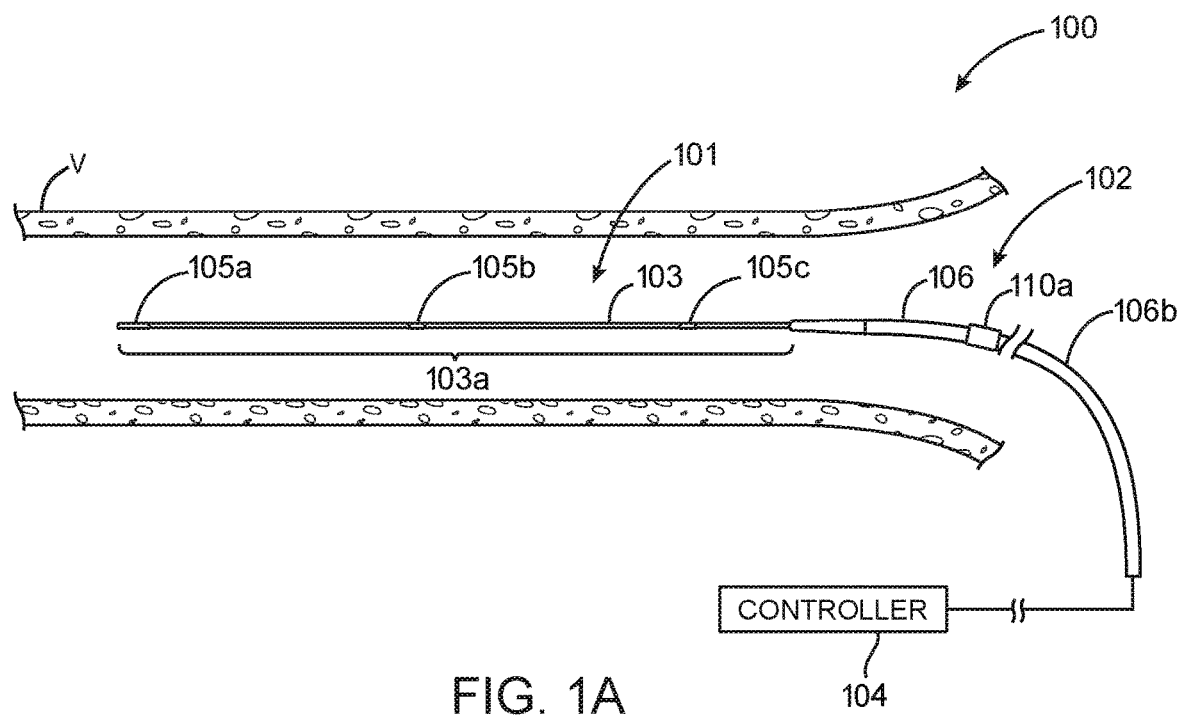
FIG. 1A is a partially schematic side view of a neuromodulation/evaluation system with a distal portion of a guidewire positioned within a blood vessel of a human patient in accordance with an embodiment of the present technology.
Figure 1B:
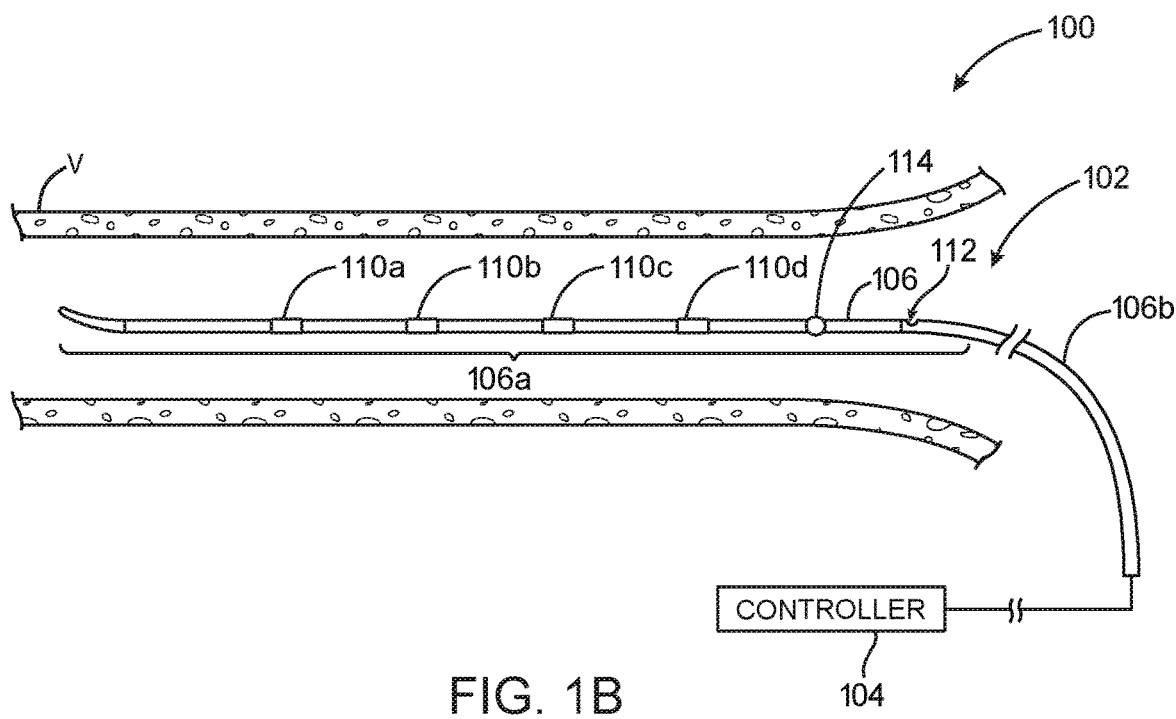
FIGS. 1B and 1C are partially schematic side views of the neuromodulation/evaluation system shown in FIG. 1A with a distal portion of a neuromodulation catheter in a first state and a second state, respectively, within a blood vessel of a human patient in accordance with an embodiment of the present technology.
Figure 1C:
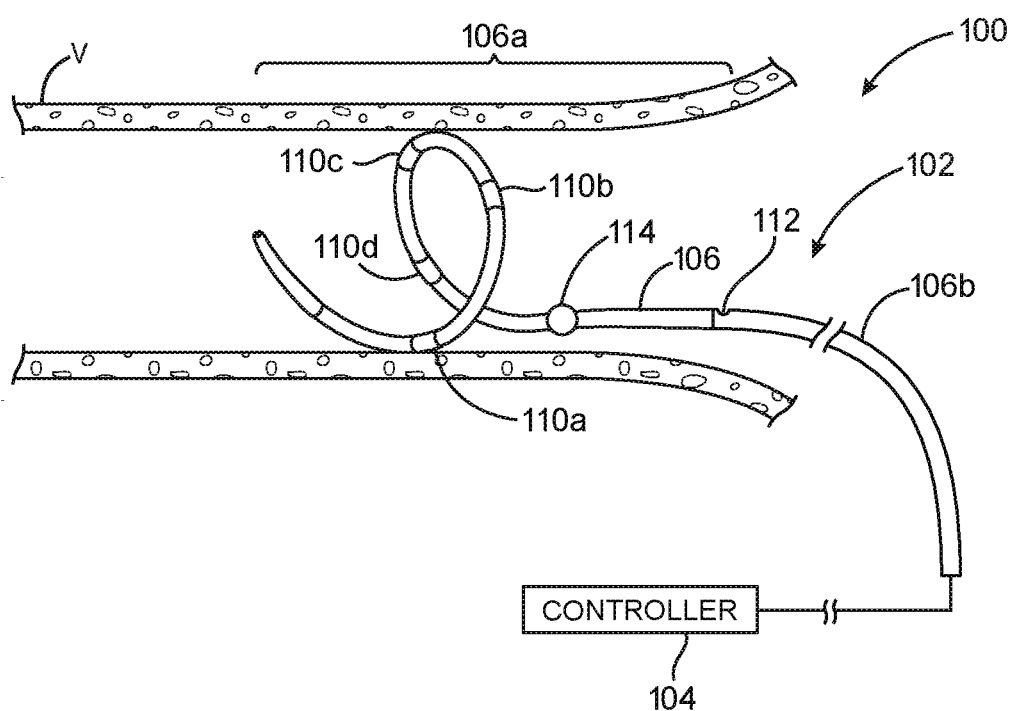

I. Selected Embodiments of Catheters and Systems for Informing and/or Evaluating Neuromodulation Therapy and Associated Methods FIGS. 1A-1C are partially schematic side views of a neuromodulation/evaluation system 100 ("system 100") configured in accordance with an embodiment of the present technology and shown in different arrangements while positioned at a target site within a blood vessel V (e.g., a renal artery) of a human patient. The system 100 includes a guidewire 101 (only visible in FIG. 1A) and a neuromodulation catheter 102 configured to perform neuromodulation at the target site to ablate nerves proximate the vessel wall. The system 100 further includes one or more controllers 104 communicatively coupled to the guidewire 101 and/or the neuromodulation catheter 102 via a wired or wireless communication link. As discussed in greater detail below, the guidewire 101 and/or the neuromodulation catheter 102 are configured to sense one or more physiological parameters before, during, and/or after the neuromodulation therapy to (1) predict a particular patient's likelihood of responding to neuromodulation therapy, and/or (2) assess the efficacy of a given neuromodulation therapy.

Referring to FIG. 1A, the guidewire 101 includes an elongated member 103 having a distal portion 103a configured to be positioned at the target site within the blood vessel V and a proximal portion (not visible) that extends outside of the patient to a handle (not shown) or other feature that allows an operator to manipulate the distal portion 103a. The guidewire 101 and/or the elongated member 103 can be sized to be slidably positioned within a lumen of the neuromodulation catheter 102. For example, in some embodiments the elongated member 103 can have an outer diameter that is less than or equal to 0.014 inches. One or more portions of the elongated member 103 can comprise a solid wire and/or a wire coil. For example, in some embodiments, the proximal portion 103b of the elongated member 103 comprises a solid wire and the distal portion 103a comprises a wire coil. In other embodiments, the elongated member 103 comprises only a solid wire or only a wire coil, and in other embodiments the elongated member 103 comprises other suitable components and/or configurations.

Additionally, the elongated member 103 can have a uniform stiffness along its length, or can have a stiffness that varies along its length.

The guidewire 101 further includes one or more sensing elements 105 (shown schematically and identified individually as 105a-105c) positioned along the distal portion 103a and configured to obtain one or more measurements related to one or more physiological parameters of the patient, such as hemodynamic parameters. Representative sensing elements 105 include one or more of the following: an electrocardiogram ("ECG") unit, a pressure sensor, a temperature sensor, a flow sensor (such as a Doppler velocity sensor or an ultrasonic flow meter), an impedance sensor, a flow rate sensor, a chemical sensor, a bio-sensing element, an electrochemical sensor, a hemodynamic sensor, an optical sensor, and/or other suitable sensing devices. Measurements obtained by the sensing elements 105 and/or physiological parameters derived from one or more measurements obtained by the sensing elements 105 include, for example: heart rate, temperature, blood pressure (e.g., systolic blood pressure, diastolic blood pressure, mean blood pressure), blood flow rate, blood velocity, blood vessel diameter, segmental volume of the blood vessel, cross-sectional area of the blood vessel, blood vessel distensibility, renal pulse wave speed, arterial (e.g., renal artery) input impedance (frequency domain), total renal artery resistance, renal artery capacitance, reflected pressure wave amplitude, augmentation index, flow reserve, resistance reserve, resistive index, capacitance reserve, hematocrit, and/or any correlates and/or derivatives of the foregoing measurements and parameters (e.g., raw data values, including voltages and/or other directly measured values). It will be appreciated that the foregoing list is merely provided for example, and in other embodiments the sensing elements 105 may be adapted to obtain additional/different parameters. In the illustrated embodiment, the guidewire 101 includes three sensing elements 105. In other embodiments, however, the guidewire 101 may include one, two, or more than three sensing elements 105. Additionally, in particular embodiments, the guidewire 101 can be a FloWire® Doppler Guide Wire (Volcano Corporation, San Diego, Calif.) or a ComboWire® XT Guide Wire (Volcano, Corporation, San Diego, Calif.).

As best shown in FIG. 1B, the neuromodulation catheter 102 includes an elongated shaft 106 configured to be slidably delivered over the guidewire 101. The elongated shaft 106 has a distal portion 106a configured to be intravascularly positioned at the target site within the blood vessel V and a proximal portion 106b extending outside of the patient to a handle (not shown) or other feature that allows an operator to manipulate the distal portion 106a of the shaft 106. As shown in FIGS. 1B and 1C, the neuromodulation catheter 102 is transformable between a first state or arrangement in which a distal portion of the neuromodulation catheter 102 is at least generally straight (FIG. 1B), and a second state or arrangement in which the distal portion of the neuromodulation catheter 102 is transformed or otherwise expanded to a spiral/helical shape (FIG. 1C).

Referring to FIGS. 1B and 1C together, the neuromodulation catheter 102 includes a plurality of energy delivery elements, such as electrodes 110 (identified individually as first through fourth electrodes 110a-110d, respectively) spaced along the distal portion 106a of the shaft 106. In the illustrated embodiment, the neuromodulation catheter 102 includes four electrodes 110. In other embodiments, however, the neuromodulation catheter 102 may include one, two, three, or more than four electrodes 110, and/or may include different energy delivery elements. The electrodes 110 are configured to deliver neuromodulation energy to the target site to modulate or ablate nerves (e.g., renal nerves) proximate to the target site. As described in greater detail below with reference to FIG. 5, the electrodes 110 and/or other features at the distal portion 106a of the shaft 106 can further be configured to apply stimuli at and/or proximate to the target site before and/or after neuromodulation, and detect a response (such as a hemodynamic response) caused by the stimuli.

In other embodiments, the neuromodulation catheter 102 can include electrodes, transducers, or other elements to delivery energy to modulate nerves using other suitable neuromodulation modalities, such as pulsed electrical energy, microwave energy, optical energy, ultrasound energy (e.g., intravascularly delivered ultrasound, extracorporeal ultrasound, and/or high-intensity focused ultrasound (HIFU)), direct heat energy, radiation (e.g., infrared, visible, and/or gamma radiation), and/or other suitable types of energy. In certain embodiments, the neuromodulation catheter 102 may be configured for cryotherapeutic treatment, and can apply cryogenic cooling to the vessel V with a refrigerant (e.g., via a balloon catheter that circulates the refrigerant). In still other embodiments, the neuromodulation catheter 102 is configured for chemical-based treatment (e.g., drug infusion), and the neuromodulation catheter 102 can apply one or more chemicals to the treatment site to effectuate neuromodulation. Such chemicals can include neurotoxins, antagonists (e.g., guanethedine), and/or tissue necrosis-inducing agents (e.g., ethyl alcohol). In such embodiments, the mode of neuromodulation (e.g., RF, ultrasound, chemical ablation, cryo-ablation) may differ from the mode of stimulation (e.g., electrical or chemical stimulation).

The dimensions (e.g., outer diameter and length) of the spiral/helical portion of the shaft 106 can be selected to accommodate the vessels or other body lumens in which the distal portion 106a of the neuromodulation catheter 102 is designed to be delivered. For example, the axial length of the spiral/helical portion of the shaft 106 may be selected to be no longer than a patient's renal artery (e.g., typically less than 7 cm), and have a diameter that accommodates the inner diameter of a typical renal artery (e.g., about 2-10 mm). In other embodiments, the spiral/helical portion of the shaft 106 can have other dimensions depending on the body lumen within which it is configured to be deployed. In further embodiments, the distal portion 106a of the shaft 106 can have other suitable shapes (e.g., semi-circular, curved, straight, etc.), and/or the neuromodulation catheter 102 can include multiple support members configured to carry one or more electrodes 110. The distal portion 106a of the shaft 106 may also be designed to apply a desired outward radial force to a vessel when expanded to the spiral/helical deployed state (shown in FIG. 1C) to place one or more of the electrodes 110 in contact with the vessel wall.

As shown in FIGS. 1B and 1C, the distal portion 106a of the neuromodulation catheter 102 can optionally include an outlet 112 configured to provide an acute injection of a pharmacological agent adapted to stimulates the vessel V or adjacent nerves to cause a hemodynamic or hyperemic response (e.g., vasodilation). In the illustrated embodiment, for example, the outlet 112 is positioned proximal to the electrodes 110 so that the pharmacological agent can flow distally through the vessel toward the electrodes 110 after injection, but in other embodiments the outlet 112 can be positioned elsewhere along the neuromodulation catheter 102 (e.g., between electrodes 110 or distal to the electrodes). The outlet 112 can be in fluid communication with a lumen (not visible) that extends through the neuromodulation catheter 102 and connects to a reservoir (not shown) of the pharmacological agent. Suitable pharmacological agents can include vasodilators, such as adenosine, bradykinin, dipyridamole, papaverine, and/or sympathetic agonists such as epinephrine, norepinephrine, Angiotensin II, and others. In the case of sympathetic agonists, the patient's lack of an immediate hemodynamic response can indicate effective ablation. In addition to or in place of direct pharmacologic stimulation, the sympathetic nervous system ("SNS"), can be stimulated by external, non-pharmacological methods, such as cold pressor stimulation (e.g., dipping the patient's hand in ice water), having the patient squeeze a rubber ball, administration of a neuropsychological stress to the patient (e.g. Stroop color test), etc. As noted above, the outlet 112 is an optional component that may not be included in some embodiments.

The neuromodulation catheter 102 can also include at least one sensing element 114 (shown schematically) and/or other device configured to detect one or more physiological parameters of the patient before, during, and/or after energy delivery. The sensing element 114 can be similar to any of the sensing elements 105 described above for use with the guidewire 101. Likewise, the measurements obtained by the sensing element 114 and/or physiological parameters derived from one or more measurements obtained by the sensing element 114 can be the same as or similar to any of the measurements and/or physiological parameters described above with respect to guidewire 101 and sensing elements 105.

Although the embodiment of the neuromodulation catheter 102 shown in FIGS. 1A-1C has a spiral/helically-shaped configuration, in other embodiments, the neuromodulation catheter can have other suitable shapes, sizes, and/or configurations. Other suitable devices and technologies are described in, for example, U.S. patent application Ser. No. 12/910,631, filed Oct. 22, 2010; U.S. patent application Ser. No. 13/279,205, filed Oct. 21, 2011; U.S. patent application Ser. No. 13/279,330, filed Oct. 23, 2011; U.S. patent application Ser. No. 13/281,360, filed Oct. 25, 2011; U.S. patent application Ser. No. 13/281,361, filed Oct. 25, 2011; PCT Application No. PCT/US11/57754, filed Oct. 25, 2011; U.S. Provisional Patent Application No. 61/646,218, filed May 5, 2012; U.S. patent application Ser. No. 13/793,647, filed Mar. 11, 2013; U.S. Provisional Patent Application No. 61/961, 874, filed Oct. 24, 2013; and U.S. patent application Ser. No. 13/670,452, filed Nov. 6, 2012. All of the foregoing applications are incorporated herein by reference in their entireties. Non-limiting examples of devices and systems include the Symplicity Flex™ catheter, the Symplicity Spyral™ multielectrode RF ablation catheter, and the Arctic Front Advance™ cardiac cryoablation system.

In some embodiments, the system 100 includes a console (not shown), and the controller 104 is integrated with the console. In such embodiments, the console can be configured to communicate with both the sensors 105 of the guidewire 101 and the neuromodulation catheter 102 via a wireless and/or wired communication link. For example, in some embodiments the console can include separate access ports for receiving a wired connection to the guidewire 101 and the neuromodulation catheter 102. In other embodiments, the console can include a single access port that can be used with both the guidewire 101 and the neuromodulation catheter 102 simultaneously or one at a time. In other embodiments, the system 100 can include two consoles; a first console configured to communicate with the guidewire 101 and a second console configured to communicate with the neuromodulation catheter 102.

A. Selected Methods for Predicting Patient Responsiveness to Neuromodulation Therapy Before delivering neuromodulation energy, it may be advantageous for the practitioner to determine one or more physiological parameters of the patient based on one or more baseline measurements. Such baseline parameters can be beneficial not only for assessing efficacy of the neuromodulation therapy, but also for identifying whether a particular patient will therapeutically benefit from neuromodulation therapy. Certain physiological parameters related to hemodynamics, for example, can be especially informative of a patient's likelihood of benefiting from neuromodulation therapy applied at a particular anatomical location. For instance, it is believed that renal artery wave speed can be a predictive marker for selecting responders to renal artery neuromodulation. In particular, a recent study found that a higher baseline renal artery wave speed correlated with a 6-month reduction in systolic blood pressure. Accordingly, the system 100 of the present technology is configured to detect and analyze one or more physiological parameters of the patient to inform the practitioner's decision to proceed with performing neuromodulation therapy.

Figure 2:
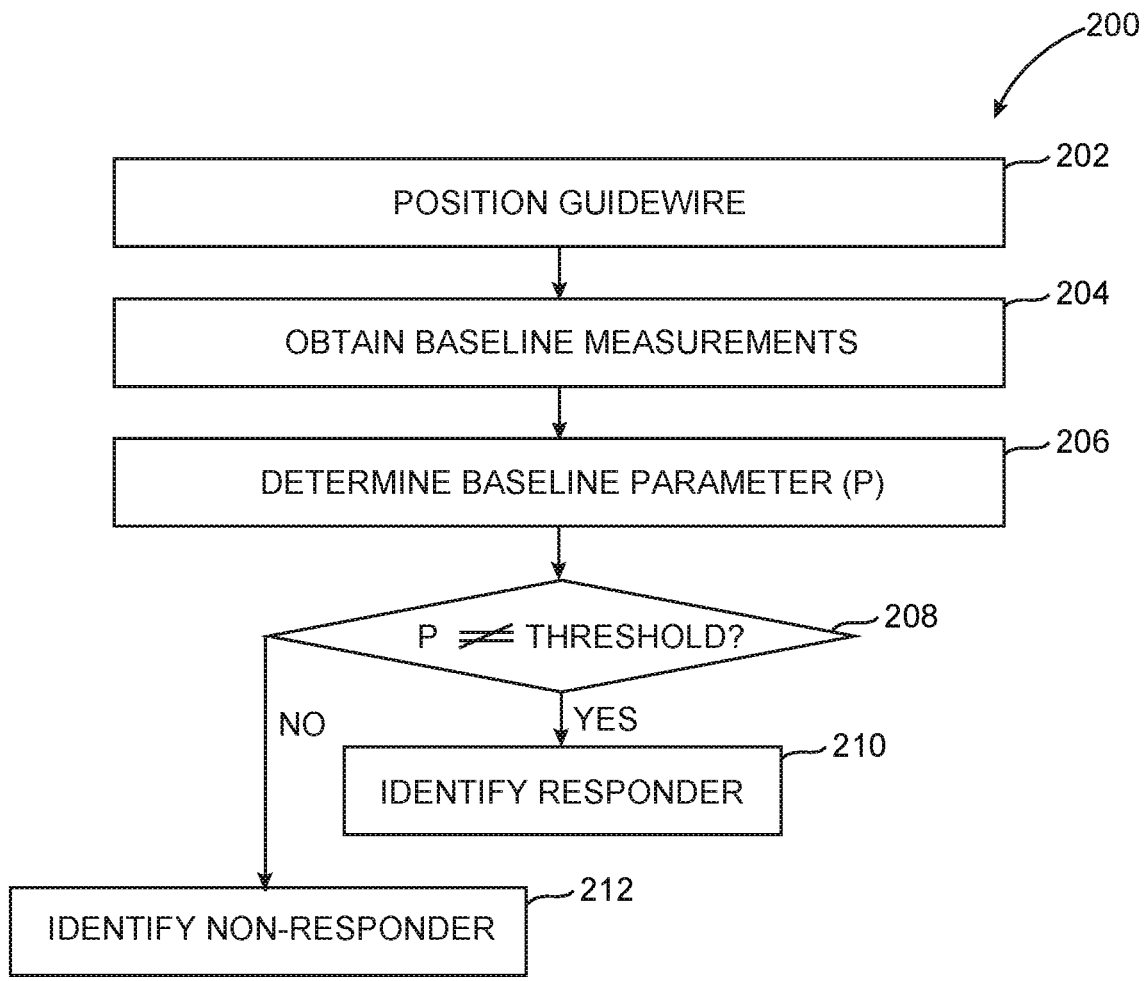
FIG. 2 is a block diagram illustrating a method for predicting patient responsiveness to neuromodulation therapy in accordance with an embodiment of the present technology.

FIG. 2 is a block diagram illustrating a method 200 for predicting patient responsiveness to neuromodulation therapy in accordance with the present technology. The method 200 can be implemented using the system 100 described above with reference to FIGS. 1A-1C and/or other suitable systems for identifying patient responders to neuromodulation therapy. As shown in FIG. 2, the method 200 includes advancing the guidewire 101 (FIG. 1A) to a target site within a blood vessel V (e.g., a renal artery) of a human patient and positioning the distal portion 103a of the guidewire 101 in a substantially straight configuration along a portion of the blood vessel V at the target site (block 202) (see FIG. 1A). While the guidewire 101 is positioned at the target site, the method 200 includes obtaining one or more measurements related to one or more physiological parameters of the patient via the sensing elements 105 (block 204) and, in some embodiments, transmitting the obtained measurements to the controller 104 and/or another feature of the system 100. The obtained measurements can then be used to determine a physiological parameter indicative of patient responsiveness to neuromodulation therapy, such as wave speed at the target site (block 206). Wave speed c can be calculated by one or more established formulas such as, for example, the "sum of squares" equation:

$$c = \frac{1}{\rho}\sqrt{\frac{\sum dP^2}{\sum dU^2}}$$

where P=pressure; U=velocity, ρ=density of blood. Wave speed c can also be estimated from pressure waveform morphometry alone (without considering velocity). It will be appreciated that other methods for determining wave speed are within the scope of the present disclosure.

The method 200 further includes comparing the physiological parameter to a predetermined threshold (block 208) to determine whether the patient is likely to therapeutically benefit from neuromodulation therapy (i.e., whether the patient is a "responder" or a "non-responder"). As used herein, the term "threshold" is used to refer to a standardized or patient-specific metric that can be a single value or range of values.

In various embodiments, comparing the determined physiological parameter to a predetermined threshold can be performed automatically by the controller 104 and/or another feature of the system 100. Based on the comparison, the controller 104 can provide the operator with an indication of whether the patient is a responder or a non-responder. For example, in an embodiment where the controller 104 calculates renal wave speed, if the renal wave speed is above or outside the predetermined threshold, the controller 104 can indicate that the patient is likely a non-responder (block 212) or has a low likelihood of benefiting from neuromodulation therapy. Additionally, in some embodiments, the controller 104 may further recommend not proceeding with neuromodulation therapy. If the renal wave speed is below or within the predetermined threshold, however, the controller 104 can indicate that the patient may be a responder (block 210), and in some embodiments may recommend proceeding with neuromodulation therapy. In particular embodiments, for example, the controller 104 can have a display that visually indicates whether the patient is a responder, such as a textual display, an indicator light, and/or other suitable indicator.

In those procedures where the baseline measurements indicate the patient is likely a responder and the operator elects to proceed with neuromodulation therapy, the operator can then advance the neuromodulation catheter 102 over the guidewire 101 to the target site, as shown in FIG. 1B. The operator can then withdraw the guidewire 101 to a position proximal of the distal portion 106a of the neuromodulation catheter 102 to deploy the neuromodulation catheter 102 (as shown in FIG. 1C) and begin delivering neuromodulation energy at the target site.

Figure 3:
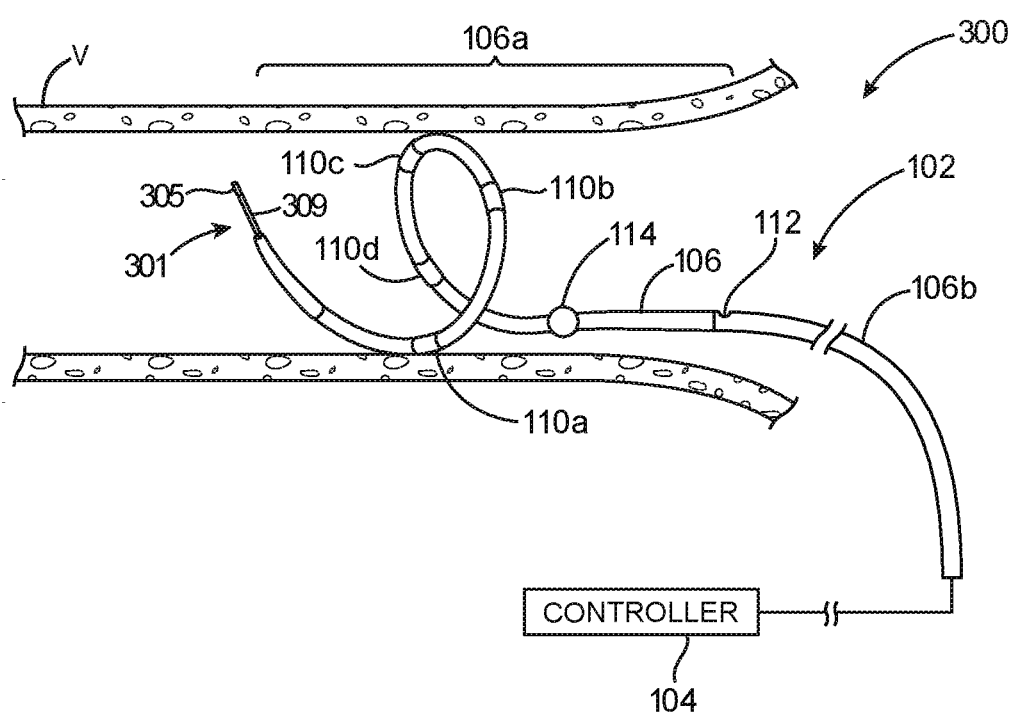
FIG. 3 is a partially schematic side view of another embodiment of a neuromodulation/evaluation system with a distal portion of a guidewire and a neuromodulation catheter positioned within a blood vessel of a human patient in accordance with an embodiment of the present technology.

In some embodiments, it may be advantageous to leave a portion of the guidewire 101 distal to the distal end of the neuromodulation catheter 102 while the neuromodulation catheter 102 is deployed so that one or more of the sensing elements 105 remain positioned in the blood vessel lumen and able to sense one or more physiological parameters. FIG. 3, for example, shows one embodiment of a system 300 configured in accordance with the present technology, shown in a deployed configuration, that includes a guidewire 301 (only the distal portion is visible) having a flexible region along its distal portion that allows the distal portion 106a of the neuromodulation catheter 102 to assume its deployed configuration while the guidewire 301 remains positioned within the lumen of the elongated shaft 106 at the distal portion 106a. To deploy the neuromodulation catheter 102, the operator can advance the neuromodulation catheter 102 over the guidewire 301 until the distal portion 106a of the neuromodulation catheter 102 is aligned with the flexible region and allowed to assume its pre-set shape. As shown in FIG. 3, a distal region 309 of the guidewire 301 remains distal to the neuromodulation catheter 102 even while the neuromodulation catheter 102 is in its deployed configuration, as does a sensing element 305 positioned along the exposed distal region 309. Accordingly, at least the exposed sensing element 305 can continue to detect one or more physiological parameters while the neuromodulation catheter 102 performs neuromodulation therapy.

In some cases it may be advantageous for the practitioner to identify one or more locations in the vessel that are better suited for efficient ablation (i.e., increased renal nerve damage with fewer lesions). To identify such locations, the practitioner may utilize one or more physiological measurements and/or parameters related to hemodynamics. For example, regions of the vessel exhibiting abnormal hemodynamics (such as turbulence and secondary flow) may not be particularly well-suited for neuromodulation therapy, and the practitioner may use such information to avoid administering neuromodulation therapy in those regions. Moreover, a comparison of the hemodynamic physiological measurements and/or parameters between two or more regions of the vessel can inform the practitioner as to whether to treat a particular portion of the vessel and/or which particular portion of the vessel to treat. For example, in some cases a low ratio of branch to main vessel flow velocity could indicate that branch treatment was less (or more) desirable.

In certain embodiments, physiological measurements or parameters may be determined at branches of a vessel (e.g., the two branch vessels that extend after the bifurcation of the renal artery) and/or at the main vessel (e.g., the renal artery), and the measurements or parameters can be compared to each other to select where to apply neuromodulation therapy. For example, a hemodynamic property (e.g., pulse wave velocity, distensibility, etc.) can be taken at two or more different regions of a vessel (e.g., a branch vessel and a main vessel, a first branch vessel and a second branch vessel, etc.) in steady state or transiently in response to a stimulus (described in further detail below). The two properties can be compared to each other and if the two values are heterogeneous, then the practitioner can elect not to apply therapeutic neuromodulation to the less responsive vessel or vessel region. Thus, even if the main vessel, branch vessel, or vessel region alone meets hemodynamic criteria for therapy, it may not be as beneficial to treat the relatively less responsive vessel or branch vessel.

In certain embodiments, the sensing element 114 of the neuromodulation catheter 102 can also be used to automatically detect one or more physiological parameters of the patient and transmit the measured values to the controller 104 for processing.

It will be appreciated that although the guidewires 101/301 and neuromodulation catheter 102 described above are configured for an "over-the-wire" delivery of the neuromodulation catheter 102, other configurations are within the scope of the present disclosure. For example, in some embodiments the neuromodulation catheter 102 and the guidewires 101/301 can be configured as a "rapid-exchange" system. In yet other embodiments, the neuromodulation catheter 102 and the guidewire 101/301 can be configured for parallel delivery. In further embodiments, the neuromodulation catheter 102 and the guidewire 101/301 can be delivered sequentially. Additionally, in some embodiments the system 100 can include a delivery sheath (not shown) configured to house the neuromodulation catheter 102 and/or the guidewire 101/301 during delivery.

B. Methods for Assessing Efficacy of Neuromodulation Therapy

It is expected that a successful or effective neuromodulation therapy (i.e., when nerves are ablated to a desired degree) causes a hemodynamic response, which can be reflected by a local and/or global change in hemodynamic physiological parameters, such as blood flow, blood pressure, and vessel diameter. As detailed below, the system 100 of the present technology is configured to detect and evaluate such changes in hemodynamic parameters before, during, and/or after neuromodulation therapy.

Figure 4:
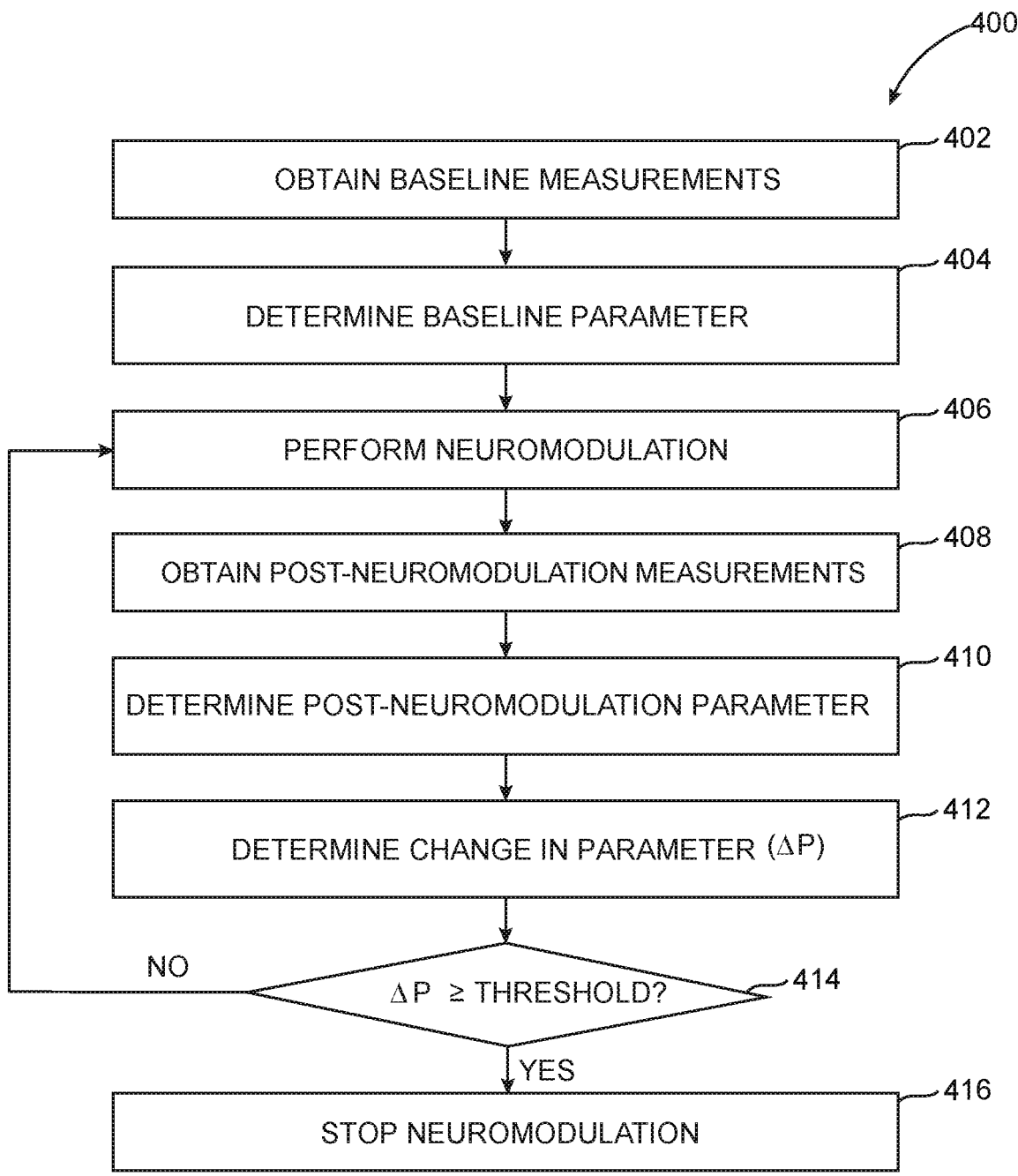
FIG. 4 is a block diagram illustrating a method of evaluating neuromodulation therapy in accordance with an embodiment of the present technology.

FIG. 4 is a block diagram illustrating a method 400 for evaluating the efficacy of neuromodulation therapy in accordance with an embodiment of the present technology. The method 400 can be implemented using the system 100 described above with reference to FIGS. 1A-1C, FIG. 3, and/or other suitable systems for evaluating the efficacy of neuromodulation therapy. For example, the guidewire 101, the neuromodulation catheter 102, and/or the controller 104 can be used to perform the various steps of the method 400. As shown in FIG. 4, the method 400 includes positioning the guidewire 101 along a portion of a blood vessel V of a human patient at a target site (see FIG. 1A) before delivering neuromodulation energy, and obtaining baseline measurements via the sensing elements 105 positioned along (or otherwise incorporated with) the guidewire 101 (block 402). The method 400 further includes communicating the obtained measurements to the controller 104, and determining one or more baseline physiological parameters (block 404) based on the obtained measurements. In some embodiments, the obtained baseline measurements and/or determined baseline physiological parameters can be stored in the controller's memory and/or another feature of the system 100. After the baseline measurements are obtained, the method 400 optionally includes utilizing the baseline measurements to determine one or more physiological parameters and comparing the determined physiological parameters to a predetermined threshold to predict whether the patient is a responder or a non-responder, as detailed above with reference to FIG. 2.

Should the operator elect to proceed with performing neuromodulation therapy, the method 400 includes advancing the neuromodulation catheter 102 over the guidewire 101 to the target site (see FIG. 1B), then withdrawing the guidewire 101 through the lumen of the neuromodulation catheter 102 at least to a position within the lumen that is proximal to the distal portion 106a of the elongated shaft 106. With the guidewire 101 withdrawn, the distal portion 106a transforms to its deployed configuration such that the electrodes 110 contact the vessel wall (see FIG. 1C). As shown at block 406, the neuromodulation catheter 102 can then perform neuromodulation at the target site to ablate nerves proximate to the vessel wall. For example, the method 400 can include applying RF energy (e.g., via electrodes), pulsed electrical energy, microwave energy, optical energy, ultrasound energy (e.g., intravascularly delivered ultrasound, extracorporeal ultrasound, and/or HIFU), direct heat energy, radiation, cryogenic cooling, chemical-based treatment, and/or another suitable type of neuromodulation energy.

After performing the neuromodulation therapy, the guidewire 101 can be advanced distally within the lumen of the elongated shaft 106, thereby transforming the distal portion 106a into a generally straight, low-profile configuration (see FIG. 1B). The neuromodulation catheter 102 can then be withdrawn from the target site to expose the distal portion 103a of the guidewire 101 (see FIG. 1A). The method 400 further includes obtaining measurements related one or more physiological parameters (block 408)—after neuromodulation therapy—via the exposed sensing elements 105 and communicating the obtained measurements to the controller 104. As shown at block 410, one or more physiological parameters can then be determined using the obtained measurements. In some embodiments, the obtained post-neuromodulation measurements and/or the determined post-neuromodulation physiological parameters can be stored by the controller's memory and/or another feature of the system 100.

The post-neuromodulation and pre-neuromodulation physiological parameters (e.g., vessel impedances, vessel diameters, etc.) can then be compared to detect a change in the respective parameter, if any, as a result of the neuromodulation therapy (block 412). In various embodiments, this comparison can be performed automatically by the controller 104 and/or another feature of the system 100. In certain embodiments, the difference between the post- and pre-neuromodulation parameters can be compared to a threshold value (block 414). The threshold value, for example, can be an equivalent to a percentage decrease (e.g., 15% less, 20% less, 50% less, 100% less, etc.) in one or more parameters (e.g., impedance, or vessel diameter, etc.), a predefined impedance or diameter value associated with effective neuromodulation, and/or a value based on other factors associated with successful neuromodulation. If the difference is greater than or equal to a predetermined threshold, the operator can elect to stop neuromodulation therapy (block 416). If the difference is less than the threshold value, the operator can elect to apply one or more additional rounds of neuromodulation energy to the treatment site using the same energy level or a higher energy level, and subsequently detect the hemodynamic response (e.g., the change in vessel impedance or diameter) as described above. Alternatively or in addition, the operator can reposition the distal portion 106a of the shaft 106 along the vessel V to apply neuromodulation energy to a different treatment site and measure the hemodynamic response (e.g., vessel impedance or diameter) at the new treatment site.

Although many hemodynamic parameters can be detected without the application of a stimulus, in certain procedures it may be beneficial to additionally or alternatively stimulate nerves at or proximate to the neuromodulation site before and after neuromodulation therapy, and detect a change in hemodynamic response caused by each stimulus. As detailed below with reference to FIG. 5, the system 100 can be configured to apply or deliver an electrical and/or pharmaceutical stimulus to a vessel to stimulate the nerves at or proximate to the target site. Stimuli, as used herein, refers to stimulations that are sufficient to evoke a neural response in nerves proximate to the vessel V (e.g., renal nerves), but not so great that they permanently affect neural functions. The stimuli can be applied proximal to the site of neuromodulation, distal to the site of neuromodulation, and/or on either side of the neuromodulation site. For example, in certain embodiments the stimuli is applied at the ostium of a vessel (e.g., the ostium of the renal artery). In other embodiments, however, the stimuli may be applied at other suitable locations.

When the nerves are functioning (i.e., conducting signals), the afferent nerves will respond to the stimulus and cause a hemodynamic response. This hemodynamic response can be measured by detecting changes in vessel dimension (e.g., diameter, cross-sectional area, and segmental volume), pressure within the vessel, blood flow through the vessel, heart rate, and/or other parameters indicative of a hemodynamic response. It is expected that the hemodynamic response to the stimulus will be eliminated or at least lessened after the nerves have been effectively ablated to a desired degree because the afferent nerves have been ablated or modulated. Accordingly, comparing the hemodynamic responses to a stimulus before and after neuromodulation is expected to indicate whether a neuromodulation treatment is successful.

Figure 5:
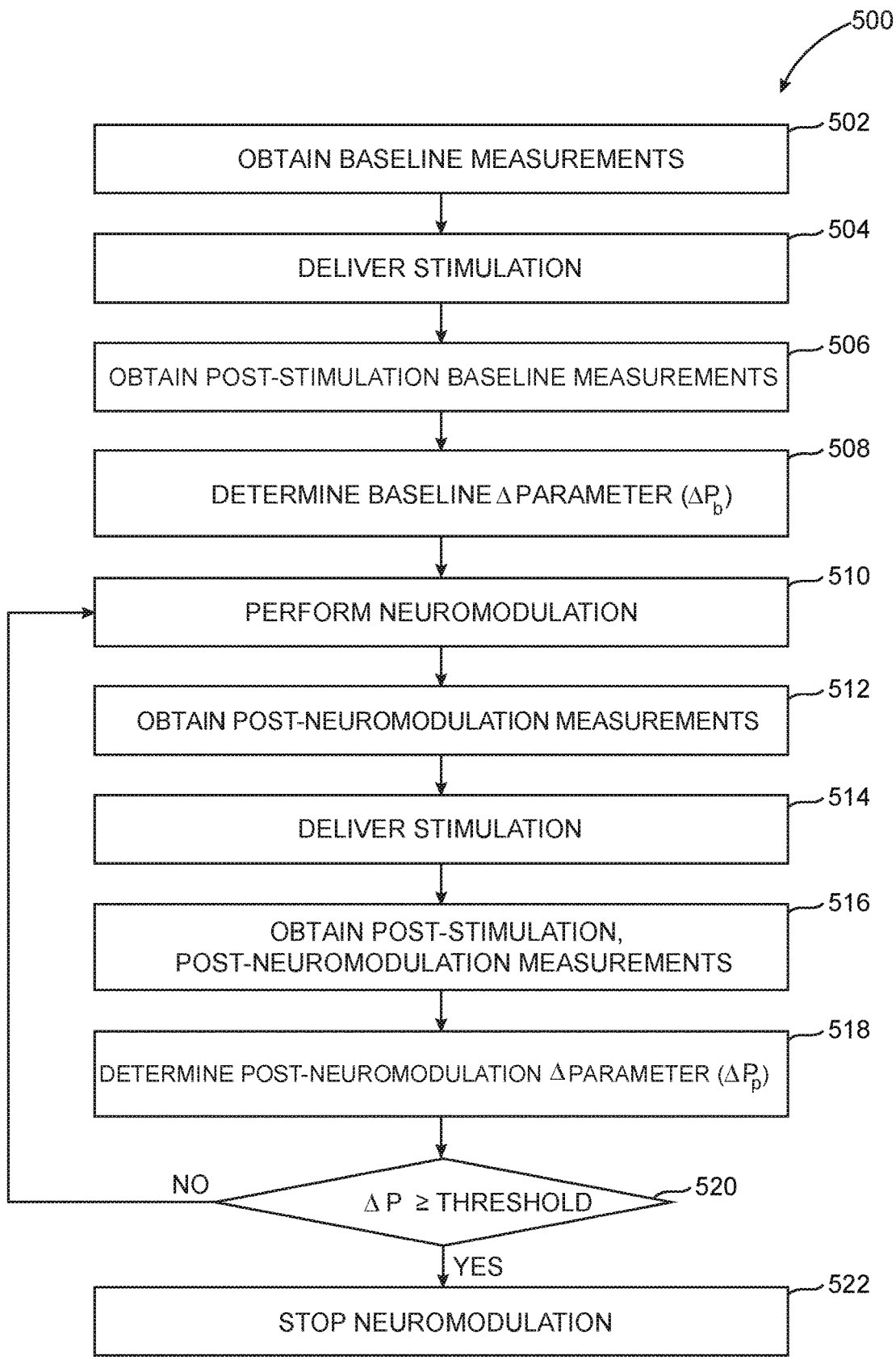
FIG. 5 is a block diagram illustrating a method of evaluating neuromodulation therapy in accordance with another embodiment of the present technology.

FIG. 5 is a block diagram illustrating a method 500 for evaluating the efficacy of neuromodulation therapy in accordance with an embodiment of the present technology. The method 500 can be implemented using the system 100 described above with reference to FIGS. 1A-1C, FIG. 3, and/or other suitable systems for evaluating the efficacy of neuromodulation therapy. For example, the guidewire 101, the neuromodulation catheter 102, and/or the controller 104 can be used to perform the various steps of the method 500. As shown in FIG. 5, the method 500 includes positioning the guidewire 101 along a portion of a blood vessel V of a human patient at a target site (see FIG. 1A) before delivering neuromodulation energy, and obtaining baseline measurements via the sensing elements 105 positioned along (or otherwise incorporated) with the guidewire 101 (block 502). Alternatively or in addition, the method 500 can include advancing the neuromodulation catheter 102 over the guidewire 101 to the target site and positioning the neuromodulation catheter 102 in a substantially straight configuration along a portion of a blood vessel V (FIG. 1B). Before delivering neuromodulation energy, the sensing element 114 of the neuromodulation catheter 102 can be used to obtain the baseline measurements.

After obtaining the baseline measurements but before applying neuromodulation energy via the electrodes, and while the neuromodulation catheter 102 is positioned in a substantially straight configuration at the target site (FIG. 1B), the electrodes 110 can apply an electrical stimulus at the target site and/or the neuromodulation catheter 102 can release a pharmacological stimulus at the treatment site via the outlet 112 (block 504). In some embodiments, the stimulus can be additionally or alternatively applied by one or more electrodes disposed at the distal portion of the guidewire 101, one or more electrodes associated with a separate catheter (e.g., positioned at or near the target site), an external sono-stimulation device, and other suitable stimulation devices and methods. The electrodes 110, sensing element 114, and/or one or more sensing elements 105 incorporated with the guidewire 101 can then obtain measurements related to the physiological parameter post-stimulation (block 506). As shown at block 508, the method 500 further includes determining a baseline metric ($\Delta P_b$) that is the difference between the corresponding measurements obtained pre-stimulation and post-stimulation.

At any time before applying neuromodulation energy, the method 500 optionally includes utilizing the baseline measurements to determine one or more physiological parameters and comparing the determined physiological parameters to a predetermined threshold to predict whether the patient is a responder or a non-responder, as detailed above with reference to FIG. 2.

Should the operator elect to proceed with performing neuromodulation therapy, the method 500 includes withdrawing the guidewire 101 through the lumen of the neuromodulation catheter 102 at least to a position within the lumen that is proximal to the distal portion 106a of the elongated shaft 106. With the guidewire 101 withdrawn, the distal portion 106a transforms to its deployed configuration such that the electrodes 110 contact the vessel wall (see FIG. 1C). As shown at block 510, the neuromodulation catheter 102 can then perform neuromodulation at the target site to ablate nerves proximate to the vessel wall. For example, the method 500 can include applying RF energy (e.g., via electrodes), pulsed electrical energy, microwave energy, optical energy, ultrasound energy (e.g., intravascularly delivered ultrasound, extracorporeal ultrasound, and/or HIFU), direct heat energy, radiation, cryogenic cooling, chemical-based treatment, and/or another suitable type of neuromodulation energy.

After performing the neuromodulation, the guidewire 101 can be advanced distally within the lumen of the elongated shaft 106, thereby transforming the distal portion 106a into a generally straight, low-profile configuration (see FIG. 1B). The method 500 further includes obtaining measurements related one or more physiological parameters (block 512)—after neuromodulation therapy—via the sensing elements 105 of the guidewire 101, the sensing element 114, and/or the electrodes 110. (A portion of the guidewire 101 may be exposed distal to the neuromodulation catheter 102 and/or the neuromodulation catheter 102 can be at least partially withdrawn from the target site to expose one or more sensing elements 105 along the guidewire 101.)

After obtaining the post-neuromodulation measurements, and while the neuromodulation catheter 102 is positioned in a substantially straight configuration at the target site (FIG. 1B), the electrodes 110 can apply an electrical stimulus at the target site and/or the neuromodulation catheter 102 can release a pharmacological stimulus at the treatment site via the outlet 112 (block 514). In some embodiments, the stimulus can be additionally or alternatively applied by one or more electrodes disposed at the distal portion of the guidewire 101, one or more electrodes associated with a separate catheter (e.g., positioned at or near the target site), an external sono-stimulation device, and other suitable stimulation devices and methods. The electrodes 110, sensing element 114, and/or one or more sensing elements 105 incorporated with the guidewire 101 can then obtain measurements related to the physiological parameter post-neuromodulation, post-stimulation (block 516). As shown at block 518, the method 500 further includes determining a post-neuromodulation metric ($\Delta P_p$) that is the difference between the corresponding measurements obtained post-neuromodulation, pre-stimulation and post-neuromodulation, post-stimulation.

A difference ($\Delta P$) between the baseline metric ($\Delta P_b$) and the post-neuromodulation metric ($\Delta P_p$) can then be compared to detect a change in the respective metric (representative of a physiological parameter), as a result of the neuromodulation therapy (block 520). In various embodiments, this comparison can be performed automatically by the controller 104 and/or another feature of the system 100. In certain embodiments, the difference between the post- and pre-neuromodulation parameters can be compared to a threshold value (block 520). The threshold, for example, can be an equivalent to a percentage decrease in the change (e.g., 15% less, 20% less, 50% less, 100% less, etc.) in one or more parameters (e.g., impedance, or vessel diameter, etc.), a predefined impedance or diameter value associated with effective neuromodulation, and/or a value based on other factors associated with successful neuromodulation. If the difference is greater than or equal to a predetermined threshold, the operator can elect to stop neuromodulation therapy (block 522). If the difference is less than the threshold value, the operator can elect to apply one or more additional rounds of neuromodulation energy to the treatment site using the same energy level or a higher energy level, and subsequently detect the hemodynamic response (e.g., the change in vessel impedance or diameter) as described above. Alternatively or in addition, the operator can reposition the distal portion 106a of the shaft 106 along the vessel V to apply neuromodulation energy to a different treatment site and measure the hemodynamic response (e.g., vessel impedance or diameter) at that new treatment site.

Other devices, systems, and methods for evaluating efficacy of neuromodulation therapy that are suitable for use with the system 100 and/or guidewire 101 of the present technology are described in PCT Application No. PCT/US15/53499, filed Oct. 1, 2015 and U.S. patent application Ser. No. 13/670,452, filed Nov. 6, 2012, both of which are incorporated herein by reference in their entireties.

Accordingly, the system 100 is expected to provide clinicians with a real time indication of nerve damage to establish whether a successful neuromodulation treatment has occurred. Thus, clinicians do not need to wait until after the procedure to determine whether the treatment was effective. Any additional energy applications necessary to effectuate neuromodulation can be performed while the neuromodulation catheter 102 is still within the vessel V. Accordingly, the system 100 can facilitate efficient and effective neuromodulation treatments.

Figure 6:
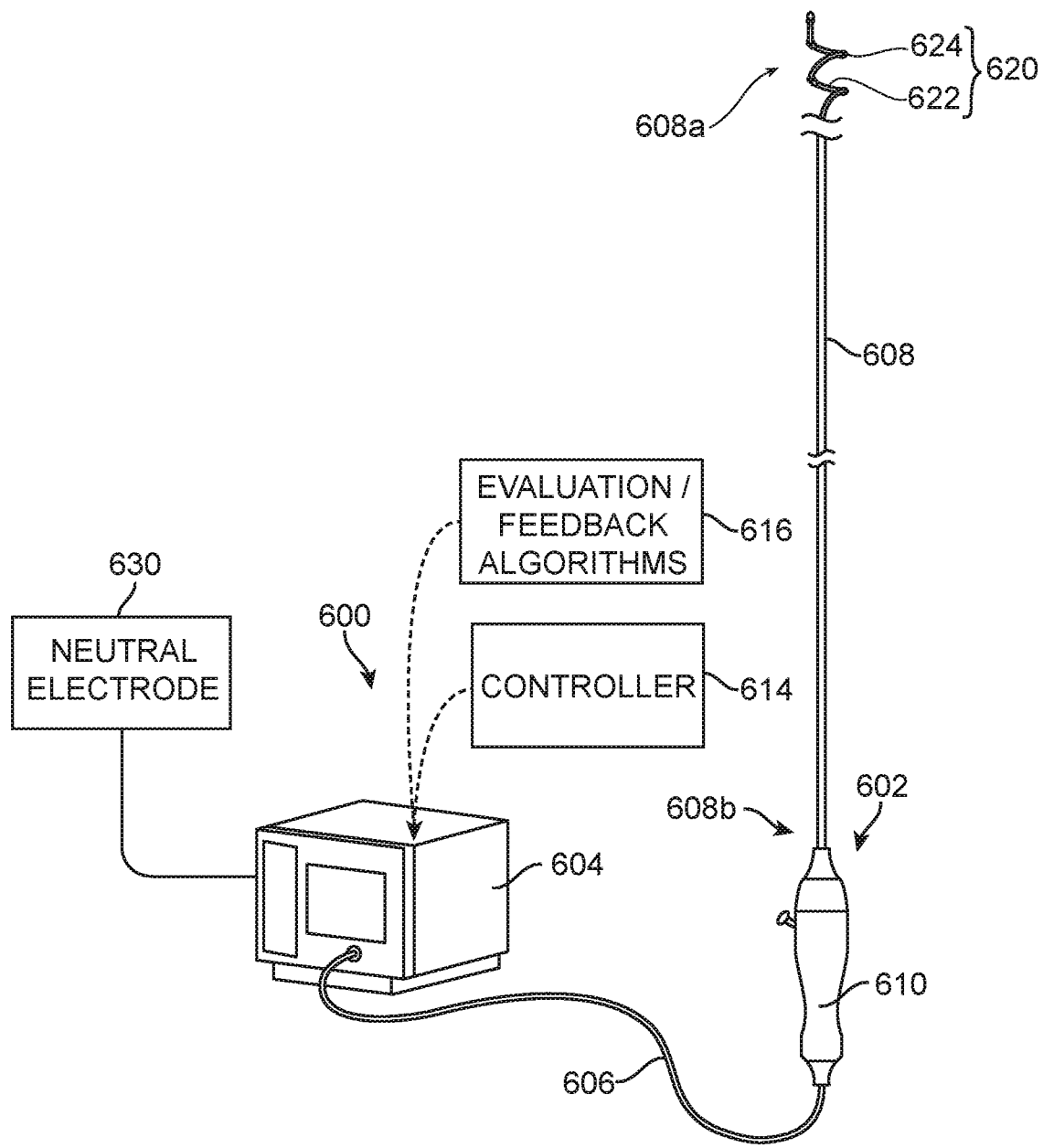
FIG. 6 is a partially schematic illustration of a neuromodulation system configured in accordance with another embodiment of the present technology.

FIG. 6 is a partially schematic illustration of a therapeutic system 600 ("system 600") configured in accordance with still another embodiment of the present technology. The system 600 can include various features similar to the systems 100 and 300 described above with respect to FIGS. 1A-1C and 3, and may be used to implement the various methods 200 and 400 described above. As shown in FIG. 6, the system 600 includes a neuromodulation catheter 602, a console 604, and a cable 606 extending therebetween. The neuromodulation catheter 602 can include an elongated shaft 608 having a proximal portion 608b, a distal portion 608a, a handle 610 operably connected to the shaft 608 at the proximal portion 608b, and a neuromodulation assembly 620 operably connected to the shaft 608 at the distal portion 608a. The shaft 608 and the neuromodulation assembly 620 can be 2, 3, 4, 5, 6, or 7 French or another suitable size. As shown in FIG. 6, the neuromodulation assembly 620 can include a support structure 622 carrying an array of two or more electrodes 624. The electrodes 624 can be configured to apply electrical stimuli (e.g., RF energy) to target sites at or proximate to vessels within a patient, temporarily stun nerves, deliver neuromodulation energy to target sites, and/or detect vessel impedance. In various embodiments, certain electrodes 624 can be dedicated to applying stimuli and/or detecting impedance, and the neuromodulation assembly 620 can include other types of therapeutic elements that provide neuromodulation therapy using various modalities, such cryotherapeutic cooling, ultrasound energy, etc.

The distal portion 608a of the shaft 608 is configured to be moved within a lumen of a human patient and locate the neuromodulation assembly 620 at a target site within or otherwise proximate to the lumen. For example, shaft 608 can be configured to position the neuromodulation assembly 620 within a blood vessel, a duct, an airway, or another naturally occurring lumen within the human body. In certain embodiments, intravascular delivery of the neuromodulation assembly 620 includes percutaneously inserting a guide wire (not shown) into a body lumen of a patient and moving the shaft 608 and/or the neuromodulation assembly 620 along the guide wire until the neuromodulation assembly 620 reaches a target site (e.g., a renal artery). For example, the distal end of the neuromodulation assembly 620 may define a passageway for engaging the guide wire for delivery of the neuromodulation assembly 620 using over-the-wire (OTW) or rapid exchange (RX) techniques. In other embodiments, the neuromodulation catheter 602 can be a steerable or non-steerable device configured for use without a guide wire. In still other embodiments, the neuromodulation catheter 602 can be configured for delivery via a guide catheter or sheath (not shown).

Once at the target site, the neuromodulation assembly 620 can be configured to apply stimuli, detect resultant hemodynamic responses, and provide or facilitate neuromodulation therapy at the target site (e.g., using the electrodes 624 and/or other energy delivery elements). For example, the neuromodulation assembly 620 can detect vessel impedance via the electrodes 624, blood flow via a flow sensing element (e.g., a Doppler velocity sensing element), local blood pressure within the vessel via a pressure transducer or other pressure sensing element, and/or other hemodynamic parameters. The detected hemodynamic responses can be transmitted to the console 604 and/or another device external to the patient. The console 604 can be configured to receive and store the recorded hemodynamic responses for further use by a clinician or operator. For example, a clinician can use the hemodynamic responses received by the console 604 to determine whether an application of neuromodulation energy was effective in modulating nerves to a desired degree.

The console 604 can be configured to control, monitor, supply, and/or otherwise support operation of the neuromodulation catheter 602. The console 604 can further be configured to generate a selected form and/or magnitude of energy for delivery to tissue at the target site via the neuromodulation assembly 620, and therefore the console 604 may have different configurations depending on the treatment modality of the neuromodulation catheter 602. For example, when the neuromodulation catheter 602 is configured for electrode-based, heat-element-based, or transducer-based treatment, the console 604 can include an energy generator (not shown) configured to generate RF energy (e.g., monopolar and/or bipolar RF energy), pulsed electrical energy, microwave energy, optical energy, ultrasound energy (e.g., intravascularly delivered ultrasound, extracorporeal ultrasound, and/or HIFU), direct heat energy, radiation (e.g., infrared, visible, and/or gamma radiation), and/or another suitable type of energy. When the neuromodulation catheter 602 is configured for cryotherapeutic treatment, the console 604 can include a refrigerant reservoir (not shown), and can be configured to supply the neuromodulation catheter 602 with refrigerant. Similarly, when the neuromodulation catheter 602 is configured for chemical-based treatment (e.g., drug infusion), the console 604 can include a chemical reservoir (not shown) and can be configured to supply the neuromodulation catheter 602 with one or more chemicals.

In selected embodiments, the system 600 may be configured to deliver a monopolar electric field via one or more of the electrodes 624. In such embodiments, a neutral or dispersive electrode 630 may be electrically connected to the console 604 and attached to the exterior of the patient. In embodiments including multiple electrodes 624, the electrodes 624 may deliver power independently (i.e., may be used in a monopolar fashion), either simultaneously, selectively, or sequentially, and/or may deliver power between any desired combination of the electrodes 624 (i.e., may be used in a bipolar fashion). In addition, an operator optionally may be permitted to choose which electrodes 624 are used for power delivery in order to form highly customized lesion(s) within the renal artery, as desired. One or more sensing elements (not shown), such as one or more temperature (e.g., thermocouple, thermistor, etc.), pressure, optical, flow, chemical, and/or other sensing elements, may be located proximate to, within, or integral with the electrodes 624. The sensing element(s) and the electrodes 624 can be connected to one or more supply wires (not shown) that transmit signals from the sensing element(s) and/or convey energy to the electrodes 624.

In various embodiments, the system 600 can further include a controller 614 communicatively coupled to the neuromodulation catheter 602. The controller 614 can be configured to initiate, terminate, and/or adjust operation of one or more components (e.g., the electrodes 624) of the neuromodulation catheter 602 directly and/or via the console 604. In other embodiments, the controller 614 can be omitted or have other suitable locations (e.g., within the handle 610, along the cable 606, etc.). The controller 614 can be configured to execute an automated control algorithm and/or to receive control instructions from an operator. Further, the console 604 can be configured to provide feedback to an operator before, during, and/or after a treatment procedure via an evaluation/feedback algorithm 616.

Figure 7:
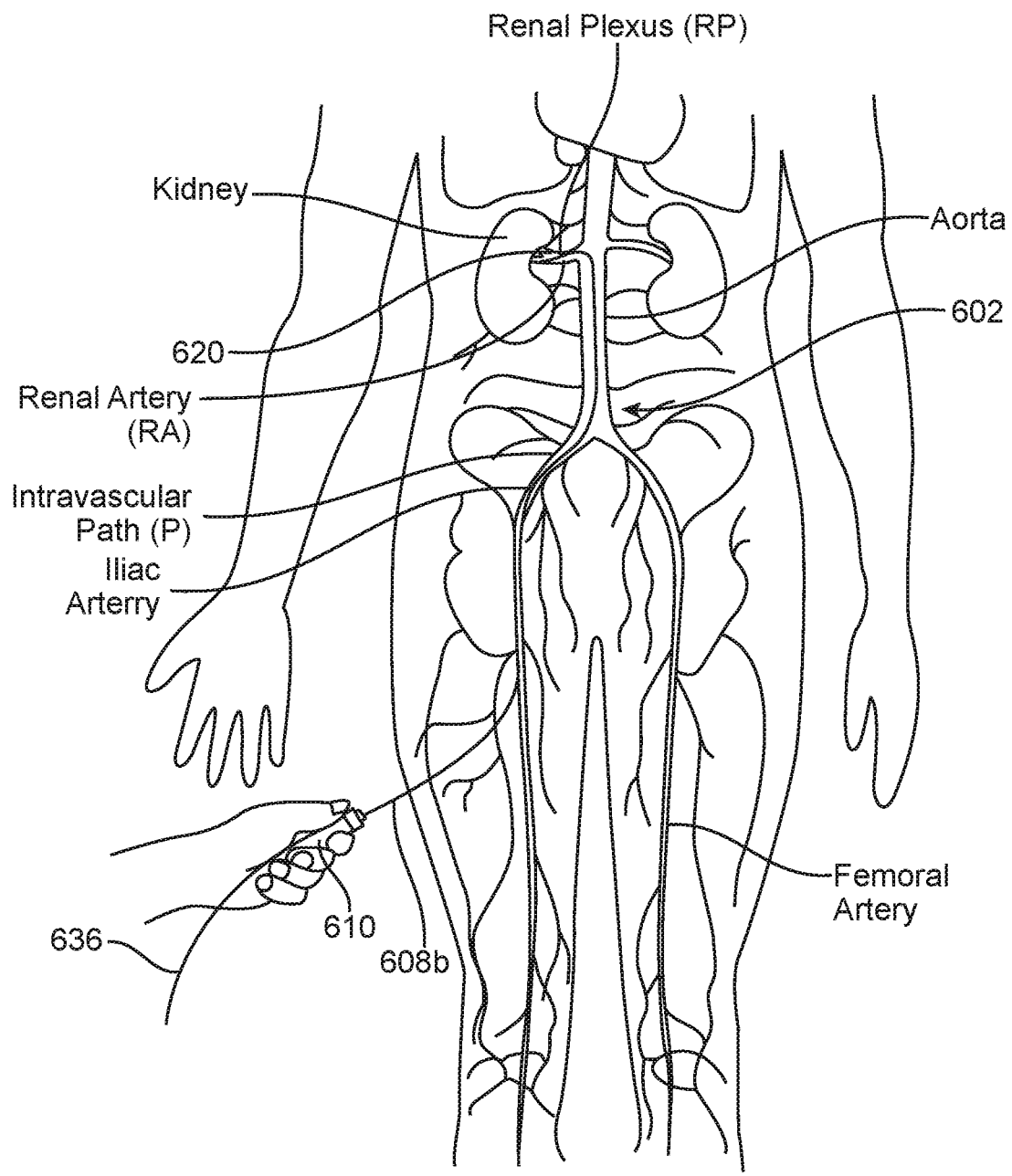
FIG. 7 illustrates modulating renal nerves and/or evaluating the neuromodulation therapy with the system of FIG. 6 in accordance with an embodiment of the present technology.

FIG. 7 (with additional reference to FIG. 6) illustrates modulating renal nerves in accordance with an embodiment of the system 600. The neuromodulation catheter 602 provides access to the renal plexus RP through an intravascular path P, such as a percutaneous access site in the femoral (illustrated), brachial, radial, or axillary artery to a targeted treatment site within a respective renal artery RA. By manipulating the proximal portion 608b of the shaft 608 from outside the intravascular path P, a clinician may advance the shaft 608 through the sometimes tortuous intravascular path P and remotely manipulate the distal portion 608a (FIG. 6) of the shaft 608. In the embodiment illustrated in FIG. 7, the neuromodulation assembly 620 is delivered intravascularly to the treatment site using a guide wire 636 in an OTW technique. As noted previously, the distal end of the neuromodulation assembly 620 may define a passageway for receiving the guide wire 636 for delivery of the neuromodulation catheter 602 using either OTW or RX techniques. At the treatment site, the guide wire 636 can be at least partially withdrawn or removed, and the neuromodulation assembly 620 can transform or otherwise be moved to a deployed arrangement for recording neural activity and/or delivering energy at the treatment site. In other embodiments, the neuromodulation assembly 620 may be delivered to the treatment site within a guide sheath (not shown) with or without using the guide wire 636. When the neuromodulation assembly 620 is at the target site, the guide sheath may be at least partially withdrawn or retracted and the neuromodulation assembly 620 can be transformed into the deployed arrangement. In still other embodiments, the shaft 608 may be steerable itself such that the neuromodulation assembly 620 may be delivered to the treatment site without the aid of the guide wire 636 and/or guide sheath.

Image guidance, e.g., computed tomography (CT), fluoroscopy, intravascular ultrasound (IVUS), optical coherence tomography (OCT), intracardiac echocardiography (ICE), or another suitable guidance modality, or combinations thereof, may be used to aid the clinician's positioning and manipulation of the neuromodulation assembly 620. For example, a fluoroscopy system (e.g., including a flat-panel detector, x-ray, or c-arm) can be rotated to accurately visualize and identify the target treatment site. In other embodiments, the treatment site can be determined using IVUS, OCT, and/or other suitable image mapping modalities that can correlate the target treatment site with an identifiable anatomical structure (e.g., a spinal feature) and/or a radiopaque ruler (e.g., positioned under or on the patient) before delivering the neuromodulation assembly 620. Further, in some embodiments, image guidance components (e.g., IVUS, OCT) may be integrated with the neuromodulation catheter 602 and/or run in parallel with the neuromodulation catheter 602 to provide image guidance during positioning of the neuromodulation assembly 620. For example, image guidance components (e.g., IVUS or OCT) can be coupled to the neuromodulation assembly 620 to provide three-dimensional images of the vasculature proximate the target site to facilitate positioning or deploying the multi-electrode assembly within the target renal blood vessel.

Energy from the electrodes 624 (FIG. 6) and/or other energy delivery elements may then be applied to target tissue to induce one or more desired neuromodulating effects on localized regions of the renal artery RA and adjacent regions of the renal plexus RP, which lay intimately within, adjacent to, or in close proximity to the adventitia of the renal artery RA. The purposeful application of the energy may achieve neuromodulation along all or at least a portion of the renal plexus RP. The neuromodulating effects are generally a function of, at least in part, power, time, contact between the energy delivery elements and the vessel wall, and blood flow through the vessel. The neuromodulating effects may include denervation, thermal ablation, and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above body temperature (e.g., approximately 37° C.) but less than about 45° C. for non-ablative thermal alteration, or the target temperature may be about 45° C. or higher for the ablative thermal alteration. Desired non-thermal neuromodulation effects may include altering the electrical signals transmitted in a nerve.

Hypothermic effects may also provide neuromodulation. For example, a cryotherapeutic applicator may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure at or near an inner surface of a renal artery wall such that proximate (e.g., adjacent) tissue is effectively cooled to a depth where sympathetic renal nerves reside. For example, the cooling structure is cooled to the extent that it causes therapeutically effective, cryogenic renal-nerve modulation. Sufficiently cooling at least a portion of a sympathetic renal nerve is expected to slow or potentially block conduction of neural signals to produce a prolonged or permanent reduction in renal sympathetic activity.

The electrodes 624 and/or other features of the neuromodulation assembly 620 can intravascularly apply stimuli to the renal artery RA and detect hemodynamic responses to the stimuli before and/or after neuromodulation energy is applied to the renal artery RA. This information can then be used to determine the efficacy of the neuromodulation therapy. For example, the controller 614 (FIG. 6) can process the detected hemodynamic responses before and after neuromodulation and compare the change in hemodynamic response to a predetermined threshold to assess whether neuromodulation therapy was effective across the treatment site or at a specific ablation site.

II. Renal Neuromodulation

Renal neuromodulation is the partial or complete incapacitation or other effective disruption of nerves of the kidneys (e.g., nerves terminating in the kidneys or in structures closely associated with the kidneys). In particular, renal neuromodulation can include inhibiting, reducing, and/or blocking neural communication along neural fibers (e.g., efferent and/or afferent neural fibers) of the kidneys. Such incapacitation can be long-term (e.g., permanent or for periods of months, years, or decades) or short-term (e.g., for periods of minutes, hours, days, or weeks). Renal neuromodulation is expected to contribute to the systemic reduction of sympathetic tone or drive and/or to benefit at least some specific organs and/or other bodily structures innervated by sympathetic nerves. Accordingly, renal neuromodulation is expected to be useful in treating clinical conditions associated with systemic sympathetic overactivity or hyperactivity, particularly conditions associated with central sympathetic overstimulation. For example, renal neuromodulation is expected to efficaciously treat hypertension, heart failure, acute myocardial infarction, metabolic syndrome, insulin resistance, diabetes, left ventricular hypertrophy, chronic and end stage renal disease, inappropriate fluid retention in heart failure, cardio-renal syndrome, polycystic kidney disease, polycystic ovary syndrome, osteoporosis, erectile dysfunction, and sudden death, among other conditions.

Renal neuromodulation can be electrically-induced, thermally-induced, chemically-induced, or induced in another suitable manner or combination of manners at one or more suitable target sites during a treatment procedure. The target site can be within or otherwise proximate to a renal lumen (e.g., a renal artery, a ureter, a renal pelvis, a major renal calyx, a minor renal calyx, or another suitable structure), and the treated tissue can include tissue at least proximate to a wall of the renal lumen. For example, with regard to a renal artery, a treatment procedure can include modulating nerves in the renal plexus, which lay intimately within or adjacent to the adventitia of the renal artery.

Renal neuromodulation can include a cryotherapeutic treatment modality alone or in combination with another treatment modality. Cryotherapeutic treatment can include cooling tissue at a target site in a manner that modulates neural function. For example, sufficiently cooling at least a portion of a sympathetic renal nerve can slow or potentially block conduction of neural signals to produce a prolonged or permanent reduction in renal sympathetic activity. This effect can occur as a result of cryotherapeutic tissue damage, which can include, for example, direct cell injury (e.g., necrosis), vascular or luminal injury (e.g., starving cells from nutrients by damaging supplying blood vessels), and/or sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Neuromodulation using a cryotherapeutic treatment in accordance with embodiments of the present technology can include cooling a structure proximate an inner surface of a body lumen wall such that tissue is effectively cooled to a depth where sympathetic renal nerves reside. For example, in some embodiments, a cooling assembly of a cryotherapeutic device can be cooled to the extent that it causes therapeutically-effective, cryogenic renal neuromodulation. In other embodiments, a cryotherapeutic treatment modality can include cooling that is not configured to cause neuromodulation. For example, the cooling can be at or above cryogenic temperatures and can be used to control neuromodulation via another treatment modality (e.g., to protect tissue from neuromodulating energy).

Renal neuromodulation can include an electrode-based or transducer-based treatment modality alone or in combination with another treatment modality. Electrode-based or transducer-based treatment can include delivering electricity and/or another form of energy to tissue at a treatment location to stimulate and/or heat the tissue in a manner that modulates neural function. For example, sufficiently stimulating and/or heating at least a portion of a sympathetic renal nerve can slow or potentially block conduction of neural signals to produce a prolonged or permanent reduction in renal sympathetic activity. A variety of suitable types of energy can be used to stimulate and/or heat tissue at a treatment location. For example, neuromodulation in accordance with embodiments of the present technology can include delivering RF energy, pulsed electrical energy, microwave energy, optical energy, focused ultrasound energy (e.g., high-intensity focused ultrasound energy), or another suitable type of energy alone or in combination. An electrode or transducer used to deliver this energy can be used alone or with other electrodes or transducers in a multi-electrode or multi-transducer array. Furthermore, the energy can be applied from within the body (e.g., within the vasculature or other body lumens in a catheter-based approach) and/or from outside the body (e.g., via an applicator positioned outside the body). Furthermore, energy can be used to reduce damage to non-targeted tissue when targeted tissue adjacent to the non-targeted tissue is subjected to neuromodulating cooling.

Neuromodulation using focused ultrasound energy (e.g., high-intensity focused ultrasound energy) can be beneficial relative to neuromodulation using other treatment modalities. Focused ultrasound is an example of a transducer-based treatment modality that can be delivered from outside the body. Focused ultrasound treatment can be performed in close association with imaging (e.g., magnetic resonance, computed tomography, fluoroscopy, ultrasound (e.g., intravascular or intraluminal), optical coherence tomography, or another suitable imaging modality). For example, imaging can be used to identify an anatomical position of a treatment location (e.g., as a set of coordinates relative to a reference point). The coordinates can then entered into a focused ultrasound device configured to change the power, angle, phase, or other suitable parameters to generate an ultrasound focal zone at the location corresponding to the coordinates. The focal zone can be small enough to localize therapeutically-effective heating at the treatment location while partially or fully avoiding potentially harmful disruption of nearby structures. To generate the focal zone, the ultrasound device can be configured to pass ultrasound energy through a lens, and/or the ultrasound energy can be generated by a curved transducer or by multiple transducers in a phased array (curved or straight).

Heating effects of electrode-based or transducer-based treatment can include ablation and/or non-ablative alteration or damage (e.g., via sustained heating and/or resistive heating). For example, a treatment procedure can include raising the temperature of target neural fibers to a target temperature above a first threshold to achieve non-ablative alteration, or above a second, higher threshold to achieve ablation. The target temperature can be higher than about body temperature (e.g., about 37° C.) but less than about 45° C. for non-ablative alteration, and the target temperature can be higher than about 45° C. for ablation. Heating tissue to a temperature between about body temperature and about 45° C. can induce non-ablative alteration, for example, via moderate heating of target neural fibers or of vascular or luminal structures that perfuse the target neural fibers. In cases where vascular structures are affected, the target neural fibers can be denied perfusion resulting in necrosis of the neural tissue. Heating tissue to a target temperature higher than about 45° C. (e.g., higher than about 60° C.) can induce ablation, for example, via substantial heating of target neural fibers or of vascular or luminal structures that perfuse the target fibers. In some patients, it can be desirable to heat tissue to temperatures that are sufficient to ablate the target neural fibers or the vascular or luminal structures, but that are less than about 90° C. (e.g., less than about 85° C., less than about 80° C., or less than about 75° C.).

Renal neuromodulation can include a chemical-based treatment modality alone or in combination with another treatment modality. Neuromodulation using chemical-based treatment can include delivering one or more chemicals (e.g., drugs or other agents) to tissue at a treatment location in a manner that modulates neural function. The chemical, for example, can be selected to affect the treatment location generally or to selectively affect some structures at the treatment location over other structures. The chemical, for example, can be guanethidine, ethanol, phenol, a neurotoxin, or another suitable agent selected to alter, damage, or disrupt nerves. A variety of suitable techniques can be used to deliver chemicals to tissue at a treatment location. For example, chemicals can be delivered via one or more needles originating outside the body or within the vasculature or other body lumens. In an intravascular example, a catheter can be used to intravascularly position a therapeutic element including a plurality of needles (e.g., microneedles) that can be retracted or otherwise blocked prior to deployment. In other embodiments, a chemical can be introduced into tissue at a treatment location via simple diffusion through a body lumen wall, electrophoresis, or another suitable mechanism. Similar techniques can be used to introduce chemicals that are not configured to cause neuromodulation, but rather to facilitate neuromodulation via another treatment modality.

III. Related Anatomy and Physiology

As noted previously, the sympathetic nervous system (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to physiological features as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

A. The Sympathetic Chain

Figure 8:
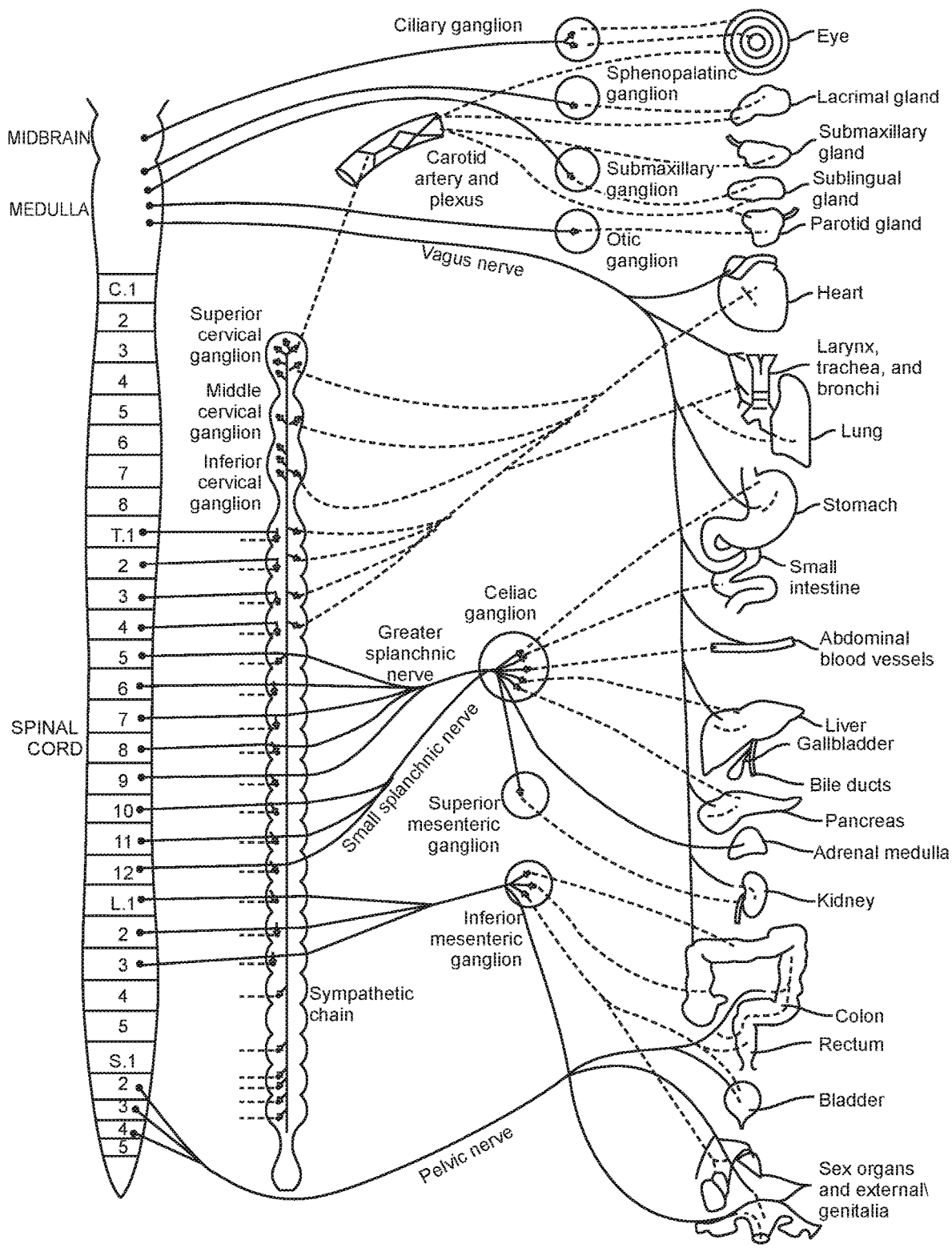
FIG. 8 is a conceptual illustration of the sympathetic nervous system (SNS) and how the brain communicates with the body via the SNS.

As shown in FIG. 8, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons should travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia, discussed above. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

1. Innervation of the Kidneys

Figure 9:
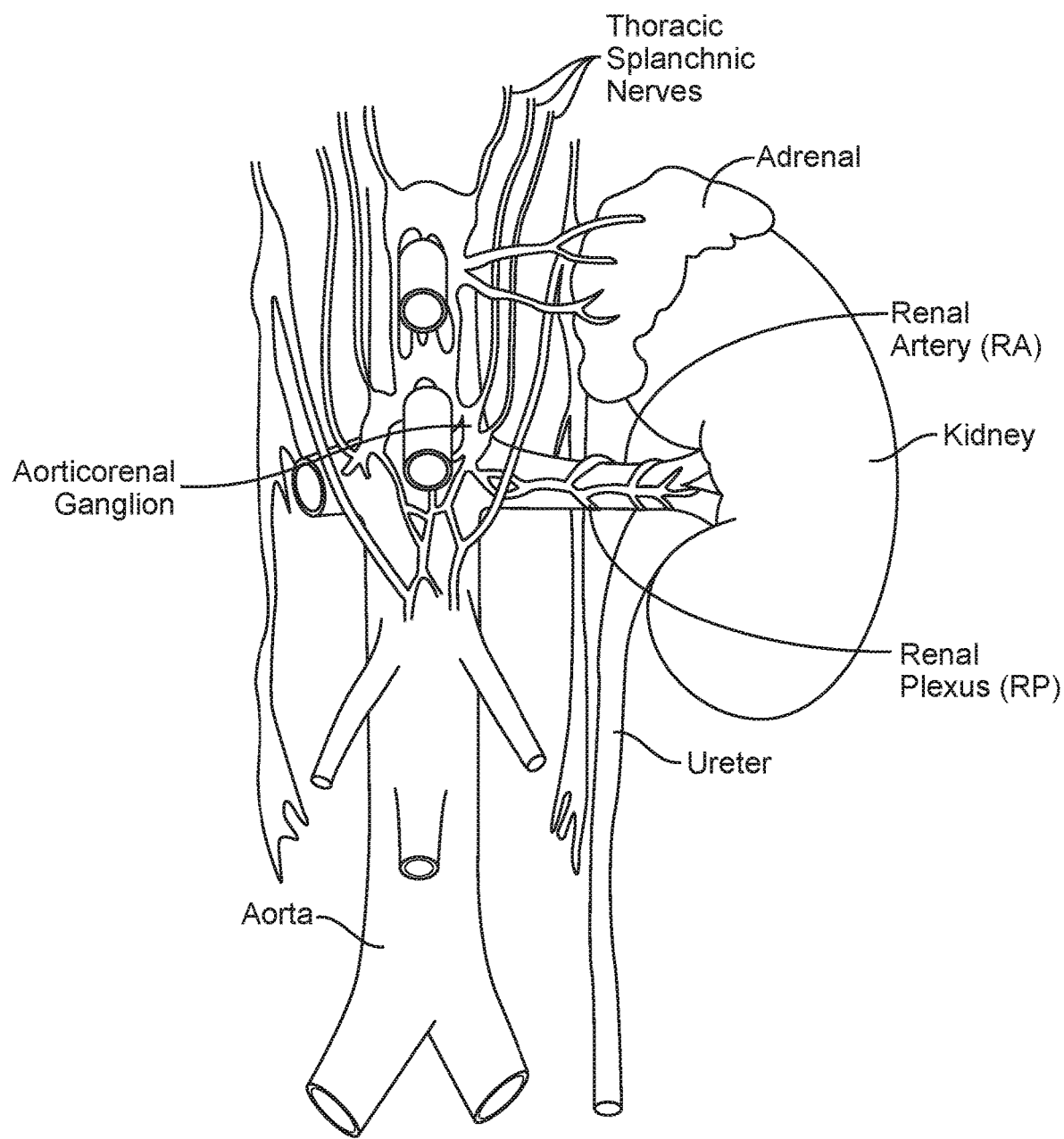
FIG. 9 is an enlarged anatomic view of nerves innervating a left kidney to form the renal plexus surrounding the left renal artery.

As FIG. 9 shows, the kidney is innervated by the renal plexus (RP), which is intimately associated with the renal artery. The renal plexus (RP) is an autonomic plexus that surrounds the renal artery and is embedded within the adventitia of the renal artery. The renal plexus (RP) extends along the renal artery until it arrives at the substance of the kidney. Fibers contributing to the renal plexus (RP) arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

2. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output, and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate, and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all-cause death and death from cardiovascular disease. This is also true for patients suffering from diabetic or contrast nephropathy. There is compelling evidence suggesting that sensory afferent signals originating from the diseased kidneys are major contributors to initiating and sustaining elevated central sympathetic outflow in this patient group; this facilitates the occurrence of the well-known adverse consequences of chronic sympathetic over activity, such as hypertension, left ventricular hypertrophy, ventricular arrhythmias, sudden cardiac death, insulin resistance, diabetes, and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium ($Na^+$) reabsorption, and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 10:
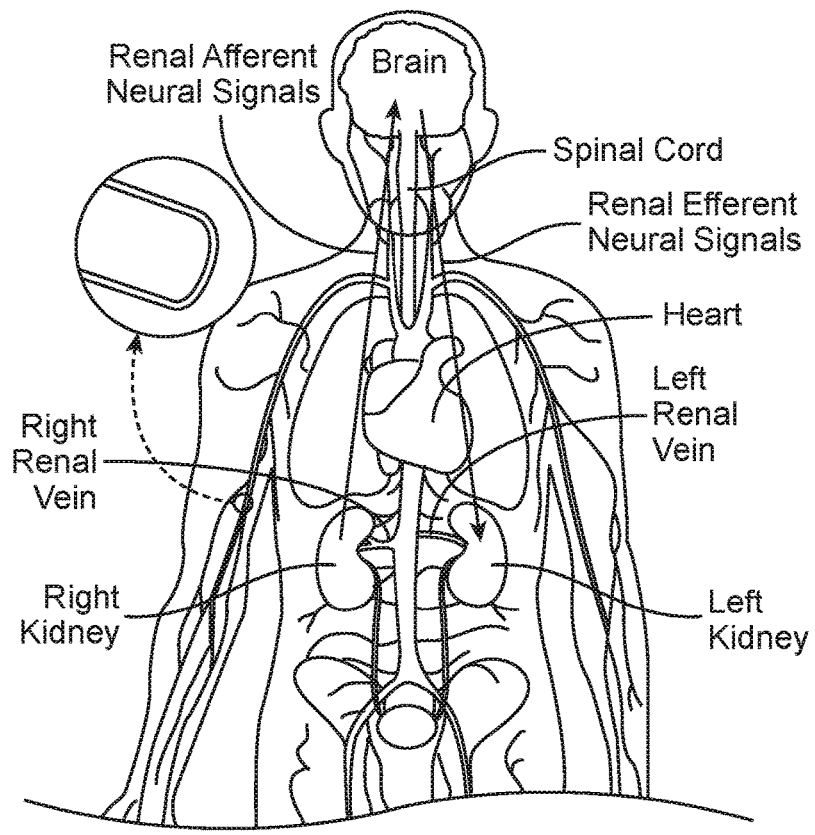
FIGS. 10 and 11 are anatomic and conceptual views, respectively, of a human body depicting neural efferent and afferent communication between the brain and kidneys.
Figure 11:
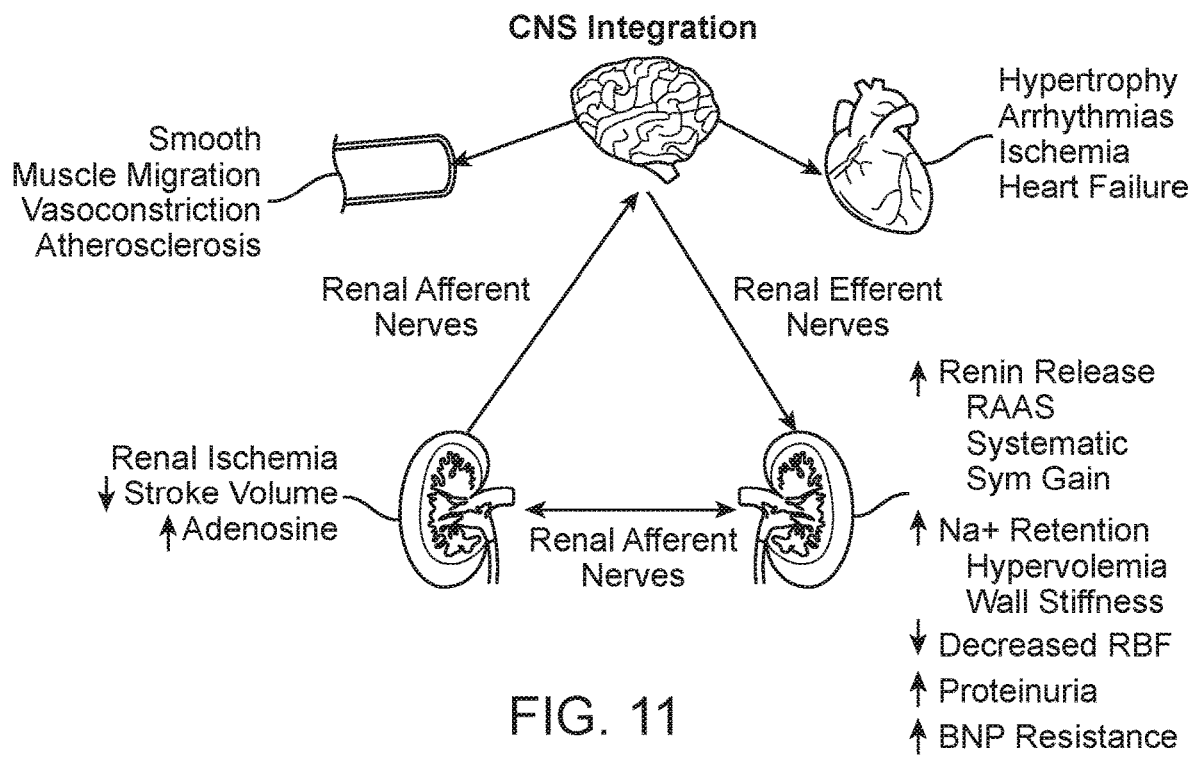

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 10 and 11, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic over activity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) modulation of tissue with efferent sympathetic nerves will reduce inappropriate renin release, salt retention, and reduction of renal blood flow, and that (ii) modulation of tissue with afferent sensory nerves will reduce the systemic contribution to hypertension and other disease states associated with increased central sympathetic tone through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic end stage renal disease, inappropriate fluid retention in heart failure, cardio-renal syndrome, and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 8. For example, as previously discussed, a reduction in central sympathetic drive may reduce the insulin resistance that afflicts people with metabolic syndrome and Type II diabetics. Additionally, patients with osteoporosis are also sympathetically activated and might also benefit from the down regulation of sympathetic drive that accompanies renal denervation.

C. Achieving Intravascular Access to the Renal Artery

Figure 12:
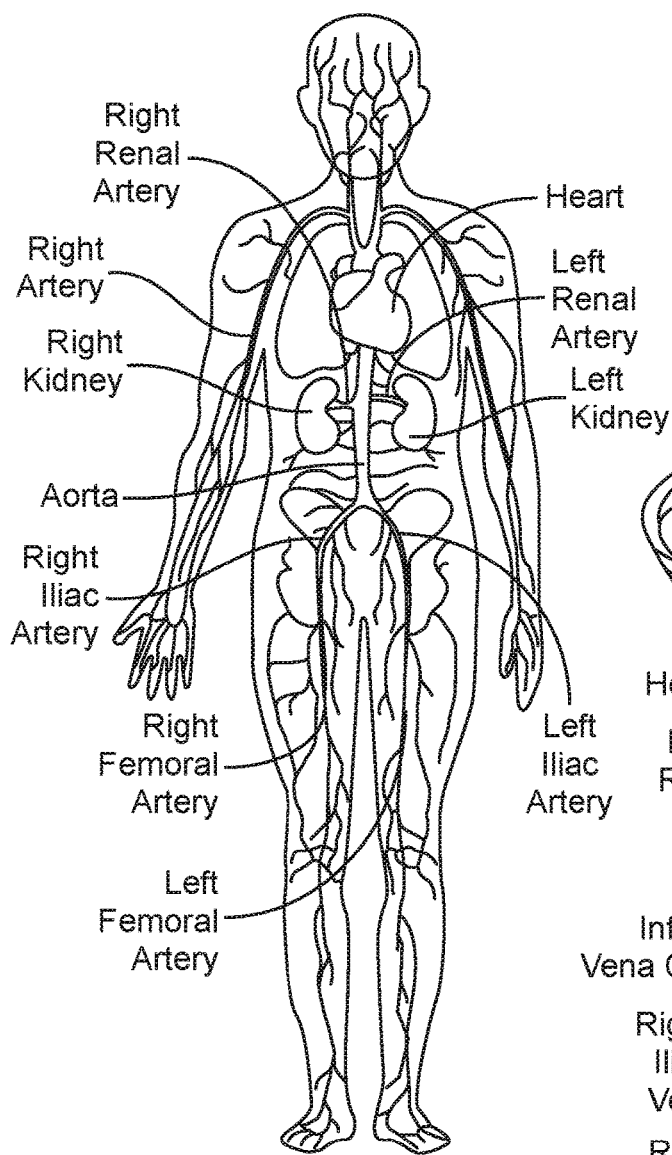
FIGS. 12 and 13 are anatomic views of the arterial vasculature and venous vasculature, respectively, of a human.

In accordance with the present technology, neuromodulation of a left and/or right renal plexus (RP), which is intimately associated with a left and/or right renal artery, may be achieved through intravascular access. As FIG. 12 shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 13:
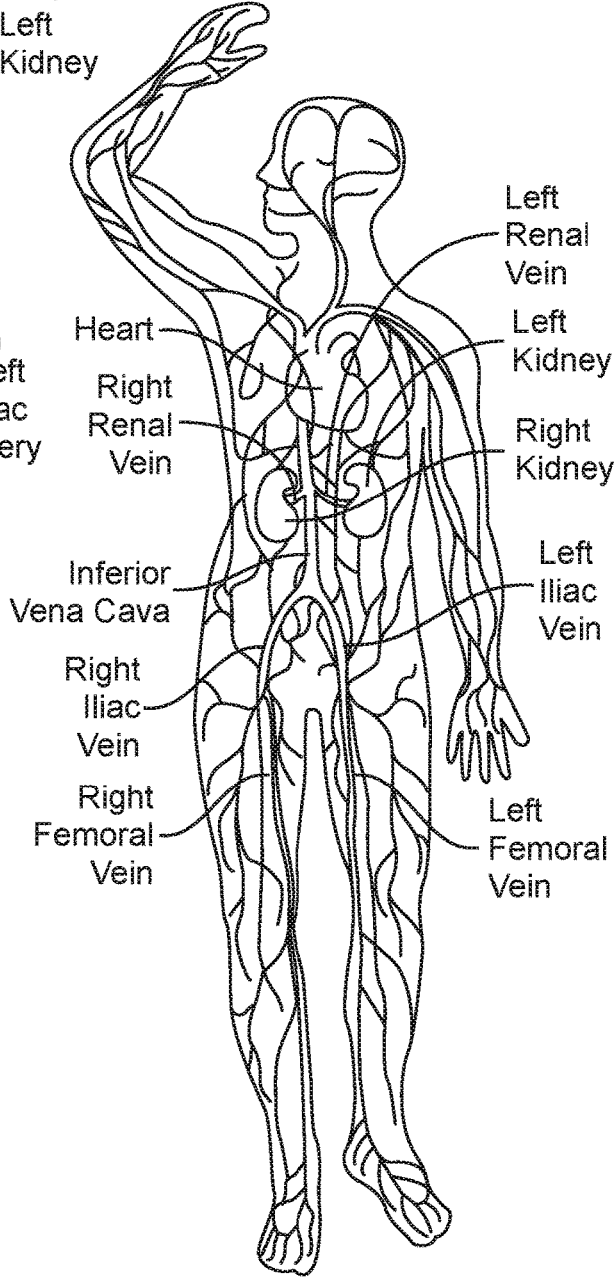

As FIG. 13 shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle just inferior to the midpoint of the inguinal ligament. A catheter may be inserted percutaneously into the femoral artery through this access site, passed through the iliac artery and aorta, and placed into either the left or right renal artery. This comprises an intravascular path that offers minimally invasive access to a respective renal artery and/or other renal blood vessels.

The wrist, upper arm, and shoulder region provide other locations for introduction of catheters into the arterial system. For example, catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems, and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained herein, may have bearing on the efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because as compared to some other arteries that are routinely accessed using catheters, the renal arteries are often extremely tortuous, may be of relatively small diameter, and/or may be of relatively short length. Furthermore, renal arterial atherosclerosis is common in many patients, particularly those with cardiovascular disease. Renal arterial anatomy also may vary significantly from patient to patient, which further complicates minimally invasive access. Significant inter-patient variation may be seen, for example, in relative tortuosity, diameter, length, and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. For example, navigation can be impeded by the tight space within a renal artery, as well as tortuosity of the artery. Furthermore, establishing consistent contact is complicated by patient movement, respiration, and/or the cardiac cycle because these factors may cause significant movement of the renal artery relative to the aorta, and the cardiac cycle may transiently distend the renal artery (i.e. cause the wall of the artery to pulse).

Even after accessing a renal artery and facilitating stable contact between neuromodulatory apparatus and a luminal surface of the artery, nerves in and around the adventitia of the artery should be safely modulated via the neuromodulatory apparatus. Effectively applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient energy should be delivered to or heat removed from the target renal nerves to modulate the target renal nerves without excessively cooling or heating the vessel wall to the extent that the wall is frozen, desiccated, or otherwise potentially affected to an undesirable extent. A potential clinical complication associated with excessive heating is thrombus formation from coagulating blood flowing through the artery. Given that this thrombus may cause a kidney infarct, thereby causing irreversible damage to the kidney, thermal treatment from within the renal artery should be applied carefully. Accordingly, the complex fluid mechanics and thermodynamic conditions present in the renal artery during treatment, particularly those that may impact heat transfer dynamics at the treatment site, may be important in applying energy (e.g., heating thermal energy) and/or removing heat from the tissue (e.g., cooling thermal conditions) from within the renal artery.

The neuromodulatory apparatus should also be configured to allow for adjustable positioning and repositioning of the energy delivery element within the renal artery since location of treatment may also impact clinical efficacy. For example, it may be tempting to apply a full circumferential treatment from within the renal artery given that the renal nerves may be spaced circumferentially around a renal artery. In some situations, a full-circle lesion likely resulting from a continuous circumferential treatment may be potentially related to renal artery stenosis. Therefore, the formation of more complex lesions along a longitudinal dimension of the renal artery and/or repositioning of the neuromodulatory apparatus to multiple treatment locations may be desirable. It should be noted, however, that a benefit of creating a circumferential ablation may outweigh the potential of renal artery stenosis or the risk may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, may contribute to dissection, perforation, denuding intima, or disrupting the interior elastic lamina.

Blood flow through a renal artery may be temporarily occluded for a short time with minimal or no complications. However, occlusion for a significant amount of time should be avoided because to prevent injury to the kidney such as ischemia. It could be beneficial to avoid occlusion all together or, if occlusion is beneficial to the embodiment, to limit the duration of occlusion, for example to 2-5 minutes.

Based on the above described challenges of (1) renal artery intervention, (2) consistent and stable placement of the treatment element against the vessel wall, (3) effective application of treatment across the vessel wall, (4) positioning and potentially repositioning the treatment apparatus to allow for multiple treatment locations, and (5) avoiding or limiting duration of blood flow occlusion, various independent and dependent properties of the renal vasculature that may be of interest include, for example, (a) vessel diameter, vessel length, intima-media thickness, coefficient of friction, and tortuosity; (b) distensibility, stiffness and modulus of elasticity of the vessel wall; (c) peak systolic, end-diastolic blood flow velocity, as well as the mean systolic-diastolic peak blood flow velocity, and mean/max volumetric blood flow rate; (d) specific heat capacity of blood and/or of the vessel wall, thermal conductivity of blood and/or of the vessel wall, and/or thermal convectivity of blood flow past a vessel wall treatment site and/or radiative heat transfer; (e) renal artery motion relative to the aorta induced by respiration, patient movement, and/or blood flow pulsatility; and (f) the take-off angle of a renal artery relative to the aorta. These properties will be discussed in greater detail with respect to the renal arteries. However, dependent on the apparatus, systems and methods utilized to achieve renal neuromodulation, such properties of the renal arteries, also may guide and/or constrain design characteristics.

As noted above, an apparatus positioned within a renal artery should conform to the geometry of the artery. Renal artery vessel diameter, DRA, typically is in a range of about 2-10 mm, with most of the patient population having a DRA of about 4 mm to about 8 mm and an average of about 6 mm. Renal artery vessel length, LRA, between its ostium at the aorta/renal artery juncture and its distal branchings, generally is in a range of about 5-70 mm, and a significant portion of the patient population is in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An additional property of the renal artery that may be of interest is the degree of renal motion relative to the aorta induced by respiration and/or blood flow pulsatility. A patient's kidney, which is located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the energy delivery element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

We claim:

1. A method for evaluating patients for neuromodulation therapy, the method comprising:
    delivering a distal portion of a neuromodulation catheter assembly to a target site within a renal blood vessel of a human patient, wherein the distal portion of the neuromodulation catheter assembly includes a sensing element;
    obtaining, via the sensing element, a first measurement related to a first hemodynamic parameter of the patient and a second measurement related to a second hemodynamic parameter of the patient;
    utilizing the first measurement and the second measurement, determining a physiological parameter indicative of patient responsiveness to renal neuromodulation therapy, wherein determining the physiological parameter comprises determining a renal wave speed;
    comparing the physiological parameter to a predetermined threshold; and
    indicating, based on the comparison, a likelihood of the patient benefitting from renal neuromodulation therapy.

2. The method of claim 1, wherein determining the physiological parameter further comprises determining a renal resistance.

3. The method of claim 1, wherein obtaining a first measurement related to the first hemodynamic parameter comprises obtaining a blood pressure measurement within the renal blood vessel.

4. The method of claim 3, wherein obtaining a second measurement related to the second hemodynamic parameter comprises obtaining a blood velocity measurement within the renal blood vessel.

5. The method of claim 4, wherein determining the renal wave speed comprises determining the renal wave speed based on the blood pressure measurement and the blood velocity measurement.

6. The method of claim 1, wherein delivering the distal portion of neuromodulation catheter assembly to the target site comprises delivering a guidewire of the neuromodulation catheter assembly to the target site, wherein the guidewire includes the sensing element.

7. The method of claim 1, further comprising, upon the physiological parameter being below or within the predetermined threshold indicating the patient will benefit from neuromodulation therapy, applying renal neuromodulation therapy to at least partially ablate nerves proximate to a wall of the renal blood vessel.

8. The method of claim 7, further comprising:
    advancing a neuromodulation catheter over a guidewire having the sensing element to the target site; and
    applying the renal neuromodulation therapy with the neuromodulation catheter.

9. The method of claim 8, further comprising:
    retracting the neuromodulation catheter; and
    obtaining post-neuromodulation measurements from the sensing element of the guidewire.

10. The method of claim 7, wherein the target site comprises a first target site and the physiological parameter comprises a first physiological parameter for the first target site, the method further comprising:
    obtaining measurements of the first and second hemodynamic parameters for a second target site;
    determining a second physiological parameter for the second target site; and
    applying the renal neuromodulation therapy to one of the first target site or the second target site based on a comparison of the first physiological parameter and the second physiological parameter.

11. The method of claim 1, wherein indicating the likelihood of the patient benefitting from renal neuromodulation therapy includes indicating the likelihood of the patient benefitting from renal neuromodulation therapy before delivering neuromodulation therapy to the target site.

12. A method for evaluating patients for neuromodulation therapy, the method comprising:
    delivering a distal portion of a neuromodulation catheter assembly to a target site within a renal blood vessel of a human patient, wherein the distal portion of the neuromodulation catheter assembly includes a sensing element;
    obtaining, via the sensing element, at least one measurement related to at least one hemodynamic parameter of the patient;

utilizing the at least one measurement, determining a physiological parameter indicative of patient responsiveness to renal neuromodulation therapy, wherein determining the physiological parameter comprises determining a renal wave speed;

comparing the physiological parameter to a predetermined threshold; and upon the comparison indicating a likelihood that the patient will benefit from renal neuromodulation therapy, applying renal neuromodulation therapy to at least partially ablate nerves proximate to a wall of the vessel.

13. The method of claim 12, wherein determining the physiological parameter further comprises determining a renal resistance.

14. The method of claim 12, wherein obtaining the at least one measurement related to at least one hemodynamic parameter comprises obtaining a blood pressure measurement within the renal blood vessel.

15. The method of claim 12, wherein obtaining the at least one measurement related to at least one hemodynamic parameter comprises obtaining a blood velocity measurement within the renal blood vessel.

16. The method of claim 12, wherein determining the renal wave speed comprises determining the renal wave speed based on a blood pressure measurement and a blood velocity measurement.

17. The method of claim 12, wherein delivering the distal portion of neuromodulation catheter assembly to the target site comprises delivering a guidewire of the neuromodulation catheter assembly to the target site, wherein the guidewire includes the sensing element.

18. The method of claim 17, further comprising:
advancing a neuromodulation catheter over a guidewire having the sensing element to the target site; and
applying the renal neuromodulation therapy with the neuromodulation catheter.

19. The method of claim 18, further comprising:
retracting the neuromodulation catheter; and
obtaining post-neuromodulation measurements from the sensing element of the guidewire.

20. The method of claim 12, wherein determining the physiological parameter indicative of patient responsiveness to renal neuromodulation therapy comprises determining the physiological parameter before delivering neuromodulation therapy to the target site.

* * * * *